US012053619B2

(12) United States Patent
McCoy et al.

(10) Patent No.: US 12,053,619 B2
(45) Date of Patent: Aug. 6, 2024

(54) INTRADERMAL JET INJECTION ELECTROPORATION

(71) Applicant: Inovio Pharmaceuticals, Inc., Plymouth Meeting, PA (US)

(72) Inventors: Jay McCoy, Temecula, CA (US); Kate Broderick, San Diego, CA (US); Stephen Vincent Kemmerrer, San Diego, CA (US)

(73) Assignee: Inovio Pharmaceuticals, Plymouth Meeting, PA (US)

( * ) Notice: Subject to any disclaimer, the term of this patent is extended or adjusted under 35 U.S.C. 154(b) by 489 days.

(21) Appl. No.: 17/314,860

(22) Filed: May 7, 2021

(65) Prior Publication Data

US 2021/0260298 A1 Aug. 26, 2021

Related U.S. Application Data

(62) Division of application No. 16/066,919, filed as application No. PCT/US2016/068972 on Dec. 28, 2016, now Pat. No. 11,027,071.

(Continued)

(51) Int. Cl.
*A61M 5/30* (2006.01)
*A61B 17/20* (2006.01)
(Continued)

(52) U.S. Cl.
CPC ............ *A61M 5/30* (2013.01); *A61B 17/205* (2013.01); *A61K 9/0021* (2013.01); *A61M 5/172* (2013.01);
(Continued)

(58) Field of Classification Search
CPC .......... A61M 5/20; A61M 5/315; A61M 5/30; A61M 5/172; A61M 5/16804;
(Continued)

(56) References Cited

U.S. PATENT DOCUMENTS 5,630,796 A 5/1997 Bellhouse et al.
5,800,399 A 9/1998 Bogert et al.
(Continued)

FOREIGN PATENT DOCUMENTS

CN 1184676 A 6/1998
CN 1345607 A 4/2002
(Continued)

OTHER PUBLICATIONS

International Preliminary Report on Patentability and Written Opinion issued in PCT/US2016/068972, dated Jul. 12, 2018.

*Primary Examiner* — Tasnim Mehjabin Ahmed
(74) *Attorney, Agent, or Firm* — BakerHostetler

(57) ABSTRACT

A jet injection and electroporation device for use with an agent cartridge defining a volume containing a pre-measured dose of agent therein, the electroporation device including a housing having an axis extend therethrough, a nozzle at least partially positioned within the housing, and a cavity sized to receive at least a portion of the agent cartridge therein. The device also includes an array having a plurality of electrodes extending therefrom, a propulsion cartridge configured to operatively engage the cartridge when the agent cartridge is positioned within the cavity; and a power supply in electrical communication with the array.

24 Claims, 18 Drawing Sheets

Related U.S. Application Data

(60) Provisional application No. 62/271,969, filed on Dec. 28, 2015.

(51) Int. Cl.
  *A61K 9/00* (2006.01)
  *A61M 5/172* (2006.01)
  *A61M 5/20* (2006.01)
  *A61M 5/24* (2006.01)
  *A61M 5/315* (2006.01)
  *A61N 1/32* (2006.01)
  *A61M 37/00* (2006.01)

(52) U.S. Cl.
  CPC .............. *A61M 5/20* (2013.01); *A61M 5/24* (2013.01); *A61M 5/315* (2013.01); *A61N 1/327* (2013.01); *A61M 2005/2013* (2013.01); *A61M 5/31511* (2013.01); *A61M 2037/0007* (2013.01); *A61M 37/0015* (2013.01); *A61M 2205/82* (2013.01)

(58) Field of Classification Search
  CPC .......... A61M 5/16831; A61M 2205/82; A61M 37/00; A61M 2037/007; A61N 1/18; A61N 1/32; A61N 1/327; A61B 17/20; A61B 17/205
  See application file for complete search history.

(56) References Cited

U.S. PATENT DOCUMENTS

| | | | |
|---|---|---|---|
| 5,911,223 A | 6/1999 | Weaver et al. | |
| 6,224,567 B1 | 5/2001 | Roser | |
| 6,309,371 B1 | 10/2001 | Deboer et al. | |
| 6,520,950 B1 | 2/2003 | Hofmann et al. | |
| 2002/0007149 A1 | 1/2002 | Nelson et al. | |
| 2003/0173110 A1 | 9/2003 | Gross et al. | |
| 2005/0215941 A1 | 9/2005 | Bernard et al. | |
| 2007/0021712 A1 | 1/2007 | Bernard et al. | |
| 2007/0021716 A1 | 1/2007 | Hansen | |
| 2007/0043320 A1 | 2/2007 | Kenany | |
| 2007/0049864 A1 | 3/2007 | Hansen | |
| 2008/0058706 A1* | 3/2008 | Zhang | A61N 1/327 604/21 |
| 2008/0091135 A1 | 4/2008 | Draghia-Akli et al. | |
| 2013/0204229 A1 | 8/2013 | Olson et al. | |
| 2014/0121587 A1 | 5/2014 | Sallberg et al. | |
| 2014/0222105 A1 | 8/2014 | Broderick et al. | |
| 2015/0088050 A1 | 3/2015 | Chang et al. | |

FOREIGN PATENT DOCUMENTS

| | | |
|---|---|---|
| CN | 1419458 A | 5/2003 |
| CN | 1651103 A | 8/2005 |
| CN | 1678369 A | 10/2005 |
| CN | 1893992 A | 1/2007 |
| CN | 101804224 A | 8/2010 |
| CN | 103687644 A | 3/2014 |
| CN | 103717249 A | 4/2014 |
| JP | 08-509604 A | 10/1996 |
| JP | 2003-529417 A | 10/2003 |
| JP | 2004-041434 A | 2/2004 |
| JP | 2005-521538 A | 7/2005 |
| JP | 2009-056339 A | 3/2009 |
| JP | 2012-223394 A | 11/2012 |
| WO | 03/86534 A1 | 10/2003 |
| WO | 2015/089492 A2 | 6/2015 |

* cited by examiner

INTRADERMAL JET INJECTION ELECTROPORATION

CROSS-REFERENCE TO RELATED APPLICATIONS

This patent application is a divisional of U.S. patent application Ser. No. 16/066,919, filed Jun. 28, 2018, now allowed, which claims priority to the National Stage Application of International Patent Application No: PCT/US2016/068972; filed Dec. 28, 2016, which claims priority to U.S. Provisional Patent Application No. 62/271,969, filed Dec. 28, 2015. The above referenced applications are hereby incorporated by reference.

BACKGROUND

The present disclosure relates to, among other things, a portable, hand-held device capable of using a needle-free jet injection and electroporation combination device to deliver an agent to a subject

SUMMARY

Needle-free jet injection enables the delivery of a drug without the use of an invasive hypodermic needle, whereby a jet of liquid is accelerated to a high speed. As a result the jet injection provides enough power for the liquid to penetrate the stratum corneum of a subject's skin.

Electroporation is the use of a transmembrane electric field pulse to induce microscopic pathways (pores) in a bio-membrane. These pores are commonly called "electropores."1 Their presence allows an agent to pass from one side of the membrane to the other. Thus, electroporation has been used to introduce drugs, DNA or other molecules into multi-cellular tissues, and may prove to be effective for the treatment of certain diseases.

There is a need in the art to provide a means for effectively delivering an agent via jet injection and subsequently being able to electroporate in a single portable, hand-held, self-contained device.

In one aspect, an electroporation device for use with an agent cartridge defining a volume containing a pre-measured dose of agent therein. The electroporation device including a housing having an axis extend therethrough, a nozzle at least partially positioned within the housing, a cavity sized to receive at least a portion of the agent cartridge therein and where the nozzle is in fluid communication with the volume of the agent cartridge when the agent cartridge is positioned within the cavity, an array having a plurality of electrodes extending therefrom, a propulsion cartridge configured to operatively engage the agent cartridge when the agent cartridge is positioned within the cavity, and a power supply in electrical communication with the array.

In another aspect, an electroporation device for use with an agent cartridge defining a volume containing a pre-measured dose of agent therein. The electroporation device including a housing defining a cavity sized to receive at least a portion of the agent cartridge therein, a nozzle at least partially positioned within the housing and in fluid communication with the agent cartridge when the cartridge is positioned within the cavity, a propulsion rod positioned at least partially within the housing and movable with respect thereto between an armed position and a deployed position, and where movement of the propulsion rod from the armed position to the deployed position expels at least a portion of the pre-measured dose of agent through the nozzle, a propulsion spring extending between the propulsion rod and the housing, the propulsion spring configured to bias the propulsion rod toward the deployed position, an array having one or more electrodes extending therefrom, a power supply, and a trigger assembly. Where the trigger assembly is adjustable between a first configuration, where the propulsion rod is fixed in the armed position and the power supply is not in electrical communication with the array, and a second position, where the propulsion rod is free to move between the armed and deployed positions and the power supply is in electrical communication with the array.

In still another aspect, an electroporation device including a cartridge defining a volume having a pre-measured dose of agent therein, at least a portion of the volume being sealed off by a plunger, and a jet injection module. The jet injection module including, a first housing defining a cavity sized to receive at least a portion of the cartridge therein, a nozzle at least partially positioned within the housing and in fluid communication with the cartridge when the cartridge is positioned within the cavity, and an array having one or more electrodes extending therefrom, where the array is movable with respect to the first housing between a retracted position, where the electrodes are positioned within the housing, and an extended position, where at least a portion of the electrodes are positioned outside the housing. The jet injection module also including a base assembly being removably couplable to the jet injection module. The base assembly including a propulsion rod positioned at least partially within the housing and movable with respect a thereto between an armed position and a deployed position, and where the propulsion rod is configured to operatively engage the cartridge, a propulsion spring extending between the propulsion rod and the housing, the propulsion spring configured to bias the propulsion rod toward the deployed position, a power supply, and a trigger assembly adjustable between a first configuration, where the propulsion rod is fixed in the armed position and the power supply is not in electrical communication with the array, and a second position, where the propulsion rod is free to move between the armed and deployed positions and the power supply is in electrical communication with the array.

DETAILED DESCRIPTION

Figure 1:
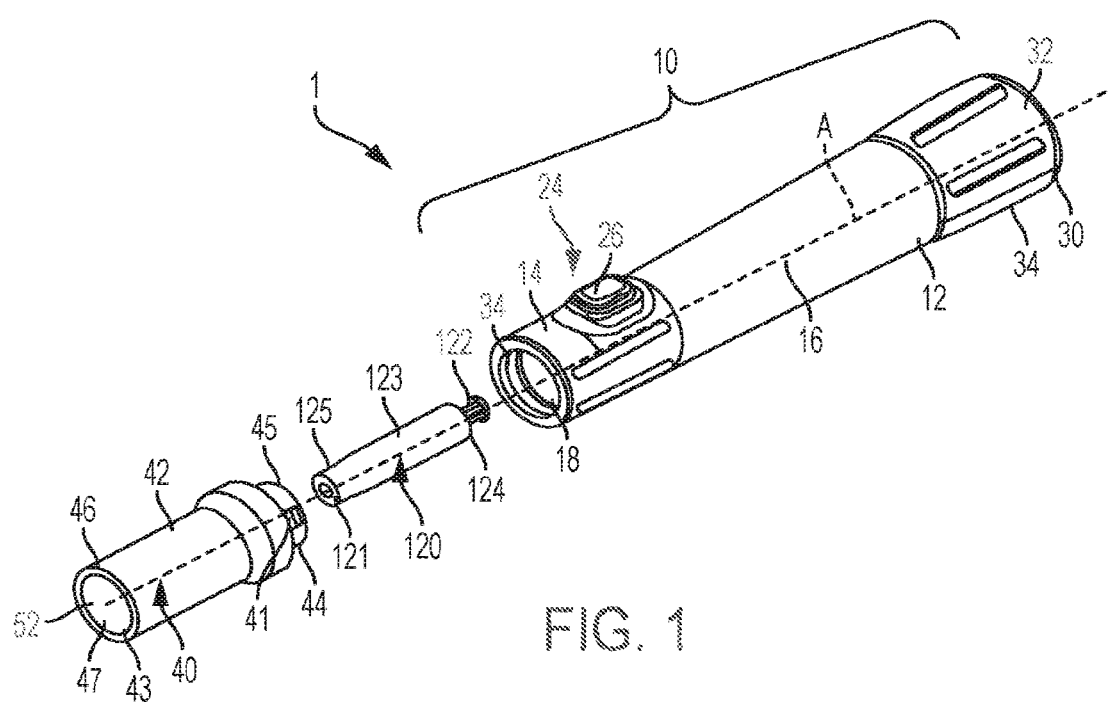
FIG. 1 is an exploded side view of a jet injection system in accordance with an embodiment of the present disclosure.

In the following detailed description, reference is made to the accompanying drawings which form a part hereof, and which are shown by way of illustration embodiments that may be practiced. It is to be understood that other embodiments may be utilized and structural or logical changes may be made without departing from the scope of the disclosure. Therefore, the following detailed description is not intended to limit the scope of the present disclosure.

The following abbreviated, or shortened, definitions are given to help the understanding of the preferred embodiments of the present disclosure. The abbreviated definitions given here are by no means exhaustive nor are they contradictory to the definitions as understood in the field or dictionary meaning. The abbreviated definitions are given here to supplement or more clearly define the definitions known in the art.

The term "current" as used herein refers to the flow or rate of flow of electric charge in a conductor or medium between two points having a difference in potential, generally expressed in amperes.

The term "ampere" as used herein refers to the standard unit for measuring the strength of an electric current. It is the rate of flow of charge in a conductor or conducting medium of one coulomb per second.

The term "coulomb" as used herein refers to the meter-kilogram-second unit of electric charge equal in magnitude to the charge of $6.28 \times 10^{18}$ electrons or the charge transported through a conductor by a current of one ampere flowing for one second.

The term "voltage" as used herein refers to the electromotive force, or difference in electrical potential, expressed in volts, which are the practical units of electromotive force or difference in potential between two points in an electric field that requires one joule of work to move a positive charge of one coulomb from the point of lower potential to the point of higher potential.

The term "power" as used herein refers to a source of physical or mechanical force or energy that is at, or can be put to, work. e.g. "electric power, water power."

The term "impedance" as used herein refers to the total opposition offered by an electric circuit to the flow of an alternating current of a single frequency. It is a combination of resistance and reactance and is measured in ohms.

The term "field" as used herein refers to physical quantity specified at points throughout a region of space.

The term "amplitude" as used herein refers to the extreme range of a fluctuating quantity, as an alternating current or the swing of a pendulum, generally measured from the average or mean to the extreme. It is the amount or degree to which a thing extends.

The term "frequency" as used herein refers to the number of periodic oscillations, vibrations, or waves per unit of time. It is usually expressed in hertz (Hz).

"Agent" may mean a polypeptide, a polynucleotide, a small molecule, a macromolecule, or any combination thereof. The agent may be a recombinant nucleic acid sequence encoding an antibody, a fragment thereof, a variant thereof, or a combination thereof, as detailed in PCT/US2014/070188, which is incorporated herein by reference. The small molecule may be a drug, for example. The drug may be chemically synthesized. "Agent" may mean a composition comprising a polypeptide, a polynucleotide, a small molecule, or any combination thereof. The composition may comprise a recombinant nucleic acid sequence encoding an antibody, a fragment thereof, a variant thereof, or a combination thereof, as detailed in PCT/US2014/070188, which is incorporated herein by reference. The agent may be formulated in water or a buffer, for example. The buffer may be saline-sodium citrate (SSC) or phosphate-buffered saline (PBS), for example. The ionic content of the buffers may increase conductivity, resulting in increased current flow in the targeted tissue. The concentration of the formulated polynucleotide may be between 1 μg and 20 mg/ml. The concentration of the formulated polynucleotide may be 1 μg/ml, 10 μg/ml, 25 μg/ml, 50 μg/ml, 100 μg/ml, 250 μg/ml, 500 μg/ml, 750 μg/ml, 1 mg/ml, 10 mg/ml, 15 mg/ml, or 20 mg/ml, for example.

A "peptide," "protein," or "polypeptide" as used herein can mean a linked sequence of amino acids and can be natural, synthetic, or a modification or combination of natural and synthetic.

"Polynucleotide" or "oligonucleotide" or "nucleic acid" as used herein means at least two nucleotides covalently linked together. A polynucleotide can be single stranded or double stranded, or can contain portions of both double stranded and single stranded sequence. The polynucleotide can be DNA, both genomic and cDNA, RNA, or a hybrid. The polynucleotide can contain combinations of deoxyribo- and ribo-nucleotides, and combinations of bases including uracil, adenine, thymine, cytosine, guanine, inosine, xanthine hypoxanthine, isocytosine, isoguanine, and synthetic or non-naturally occurring nucleotides and nucleosides. Polynucleotides may be a vector. Polynucleotides can be obtained by chemical synthesis methods or by recombinant methods. The polynucleotide may be a siRNA.

"Vector" as used herein means a nucleic acid sequence containing an origin of replication. A vector can be a viral vector, bacteriophage, bacterial artificial chromosome, or yeast artificial chromosome. A vector can be a DNA or RNA vector. A vector can be a self-replicating extrachromosomal vector, and preferably, is a DNA plasmid.

The term "macromolecule" as used herein may refer to nucleic acid sequences, proteins, lipids, microbubbles (e.g. drug-loaded vesicles), and pharmaceuticals, for example.

The term "electroporation," ("EP") as used herein refers to the use of an electric field pulse to induce reversible microscopic pathways (pores) in a bio-membrane; their presence allows agents to pass from one side of the cellular membrane to the other.

The term "skin region" as used herein refers to skin tissue, dermis, epidermis, and intradermic ("ID"), including the region between the stratum corneum and basal layers. The skin region does not include muscle tissue.

The term "needle-free injection" as used herein refers to the injection of an agent into tissue without the use of a needle, for example as a small stream or jet, with such force that the agent pierces the surface of the tissue and enters underlying tissue. In one embodiment, the injector creates a very high-speed jet of liquid that substantially painlessly pierces the tissue. Such needle-free injectors are commercially available and can be used by those having ordinary skill in the art to introduce agents (i.e. by injection) into tissues of a subject.

The term "minimally invasive" as used herein refers to a limited penetration by the needle electrodes of embodiments of an electroporation device, and can include noninvasive electrodes (or nonpenetrating needles). The penetration is to a degree that penetrates through stratum corneum, and preferably enters into the outer most living tissue layer, the stratum granulosum, but does not penetrate the basal layer. The penetration depth is not to exceed 1.0 mm, and can be a depth ranging from about 0.01 mm to about 1.0 mm and in particular from about 0.01 mm to about 0.04 mm to break through stratum corneum. This can be accomplished using an electrode that allows penetration through the stratum corneum but avoids deep penetration.

The present disclosure relates to the introduction of a desired agent in a form suitable for direct or indirect electrotransport (e.g., injected) using a needle-free injector into the tissue to be treated, usually by contacting the tissue surface with the injector so as to actuate delivery of a jet of the agent, with sufficient force to cause penetration of the agent into the skin region, for example, to penetrate through the stratum corneum and into dermal layers.

The present disclosure also pertains to a needle-free device, in particular a handheld and portable device, for providing an electric field through an electrode needle array and facilitating the introduction of an agent into cells of a selected tissue in a body, in particular skin. The needle-free device produces a current waveform (e.g., a pulse train) that passes through the electrodes of the electrode needle array in accordance with a programmed sequence and can be monitored and recorded during the procedure. The electrodes are capable of contacting the skin region without substantially penetrating a muscle tissue. FIGS. 1-11 illustrate a device that can be operable for use in both clinical and commercial environments to administer medical treatment to a patient in the form of jet injection and electroporation. Specifically, FIGS. 1 and 3 illustrate a device that can be operable to administer medical treatment to a patient in the form of jet injection. FIGS. 5, 6, 7A, 7B, and 9 illustrate a combination device that can be operable to administer medical treatment to a patient in the form of jet injection and electroporation. The jet injection module and the electroporation array assembly are coaxially aligned, which decreases the likelihood of error in electroporating the incorrect area. In addition, the electrode array assembly of the present disclosure is retractable, which permits the formation of a bleb/wheal during the jet injection while allowing electroporation immediately upon bleb formation. It may also be possible to use the combination device as an electroporating module, without utilizing the jet injection function, as explained in greater detail below.

As illustrated in FIGS. 1-20, the present disclosure includes a needle-free injection system 1 including a base assembly 10 and a jet injection module 40. The base assembly 10 has an upper end 12, a lower end 14, and a longitudinal axis extending therebetween which defines a first axis A The base assembly 10 includes a housing 16, a trigger assembly 24, and a rotational knob 30. The housing 16 defines a cavity 18 configured to receive a propulsion cartridge 60, as described in greater detail below. The rotational knob 30 is positioned at an upper end 12 of the base assembly 10. The rotational knob 30 has an upper portion 32 and a lower portion 34 that are configured to be coupled by fasteners 33. Illustrated in FIGS. 1 and 2, the upper and lower portions 32, 34 may be coupled to define an interior portion configured to operably couple to the propulsion cartridge 60, as explained in further detail below.

Figure 2:
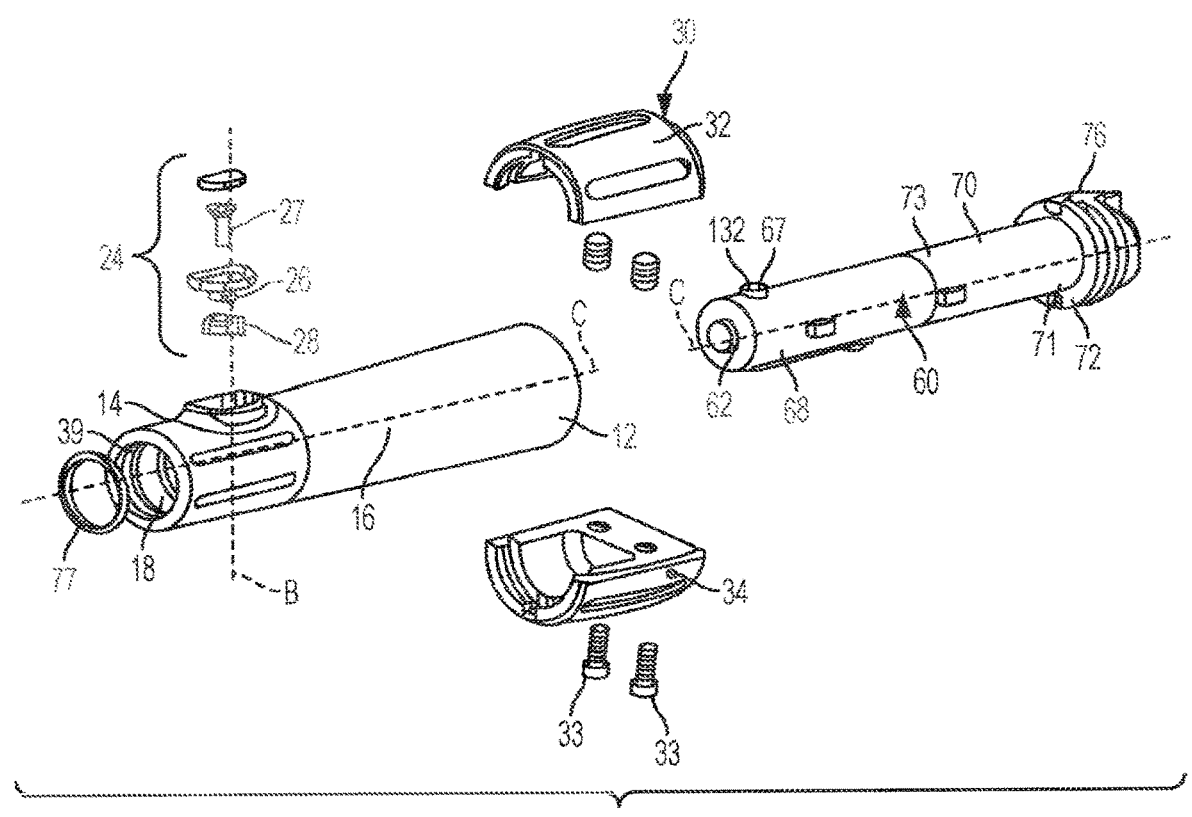
FIG. 2 is an exploded side view of a base assembly (as well as an embodiment of a propulsion cartridge) in accordance with an embodiment of the present disclosure.
Figure 3:
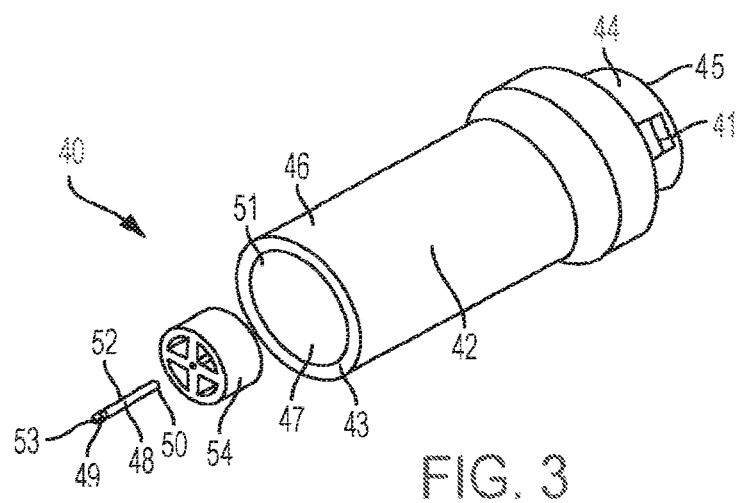
FIG. 3 is an exploded side view of a jet injection module in accordance with an embodiment of the present disclosure.
Figure 12:
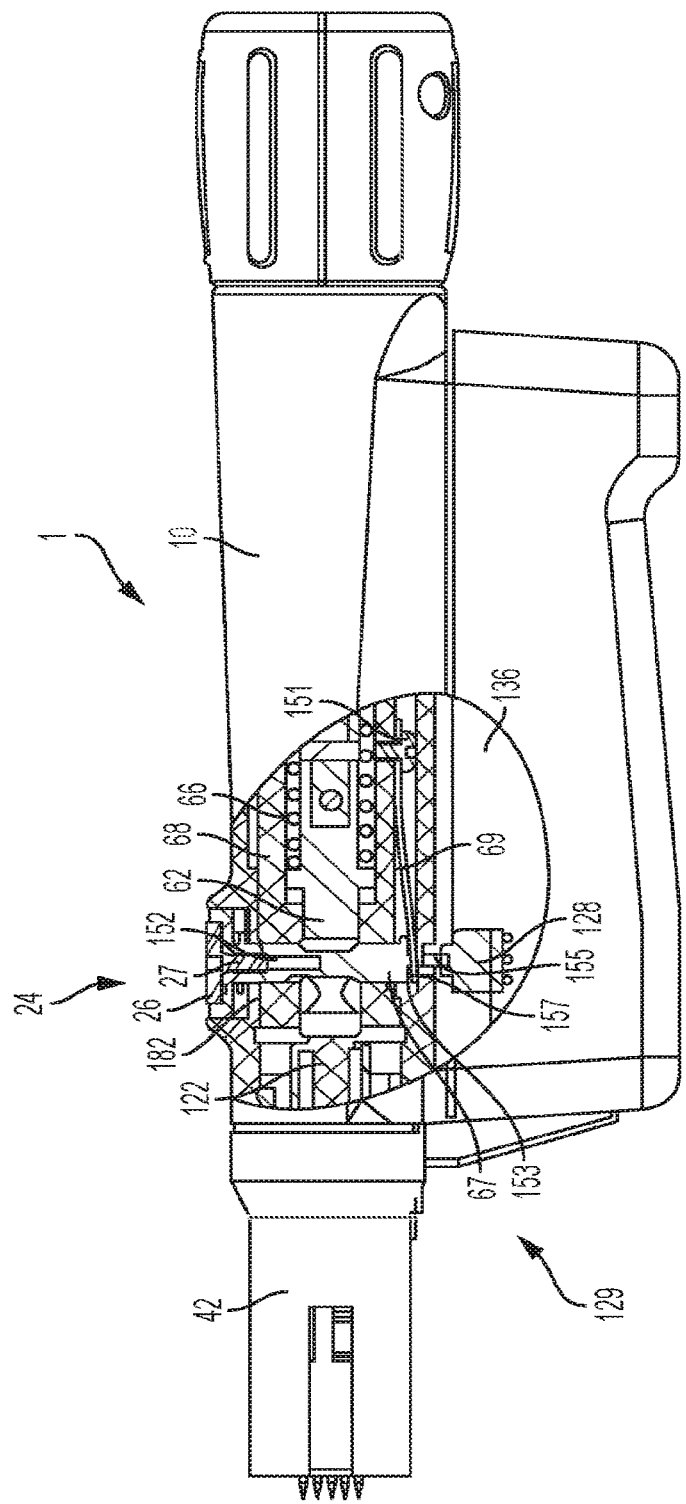
FIG. 12 is a partial cross-sectional view of a jet injection and EP combination device in accordance with an embodiment of the present disclosure.

FIGS. 2 and 12 illustrate the trigger assembly 24 of the base assembly 10. The trigger assembly 24 may be positioned anywhere along the length of the base assembly 10. In the illustrated embodiment of FIG. 1, the trigger assembly 24 is positioned at the lower end 14 of the housing 16. The trigger assembly 24 includes a trigger spring 28, a trigger post 27, and a push button 26 configured to actuate the system 1, as explained in further detail below. The push button 26 is configured to fit into the housing 16 such that the push button 26 may travel from a first position, illustrated in FIG. 1, to a second, depressed position (e.g., depressed within the housing 16). The direction of travel from the first position to the second position may define a second axis B. In the embodiment illustrated in FIGS. 1 and 2, the second axis Bis generally perpendicular to the first axis A. The trigger spring 28 urges the push button 26 toward the first position. The trigger post 27 operatively couples the trigger assembly 24 to a channel 152 of a trigger pin 67, as explained in further detail below. Furthermore, the trigger assembly 24 may be in electrical communication with the electroporation components, as also explained in further detail below. The trigger assembly 24 may be positioned behind a protective diaphragm (e.g., a plastic and/or gel covering; not illustrated) providing both an ergonomic feel and fluid ingress protection.

Figure 4:
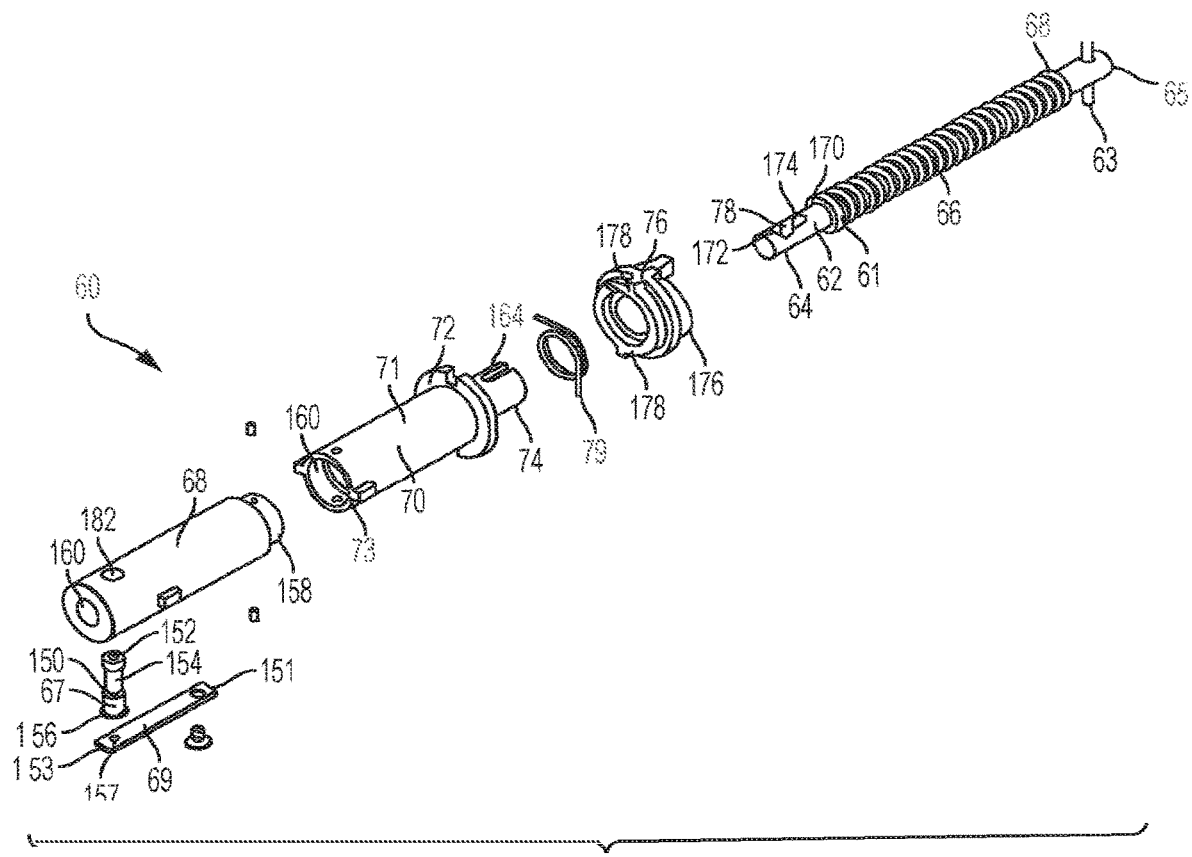
FIG. 4 is an exploded side view of a propulsion cartridge in accordance with an embodiment of the present disclosure.
Figure 17:
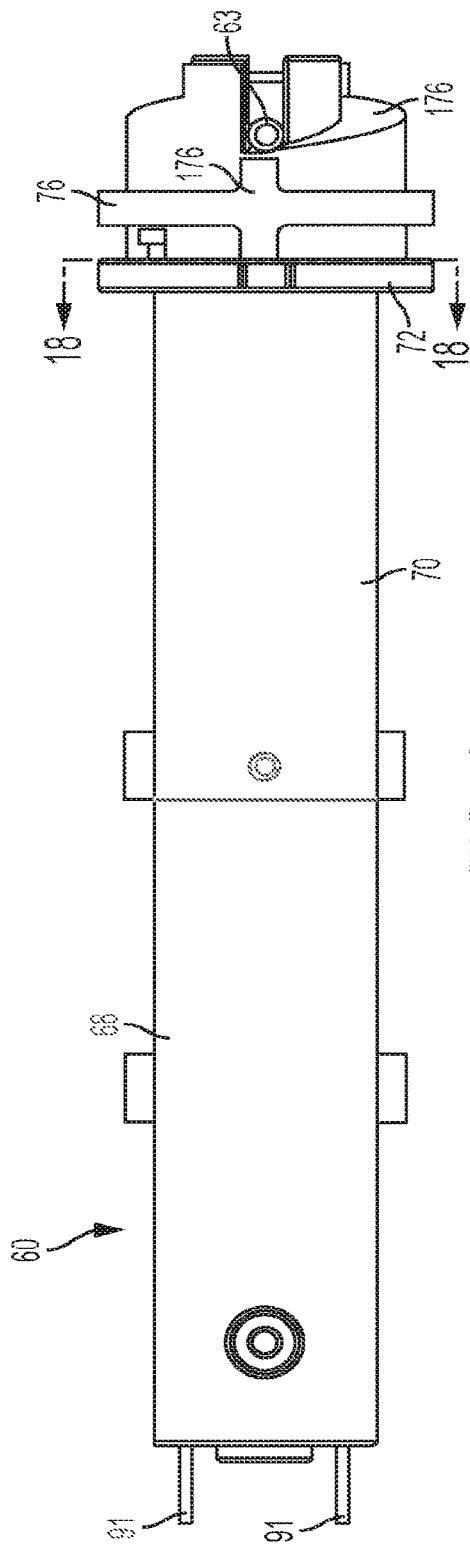
FIG. 17 is a perspective view of a propulsion cartridge in accordance with an embodiment of the present disclosure.
Figure 19:
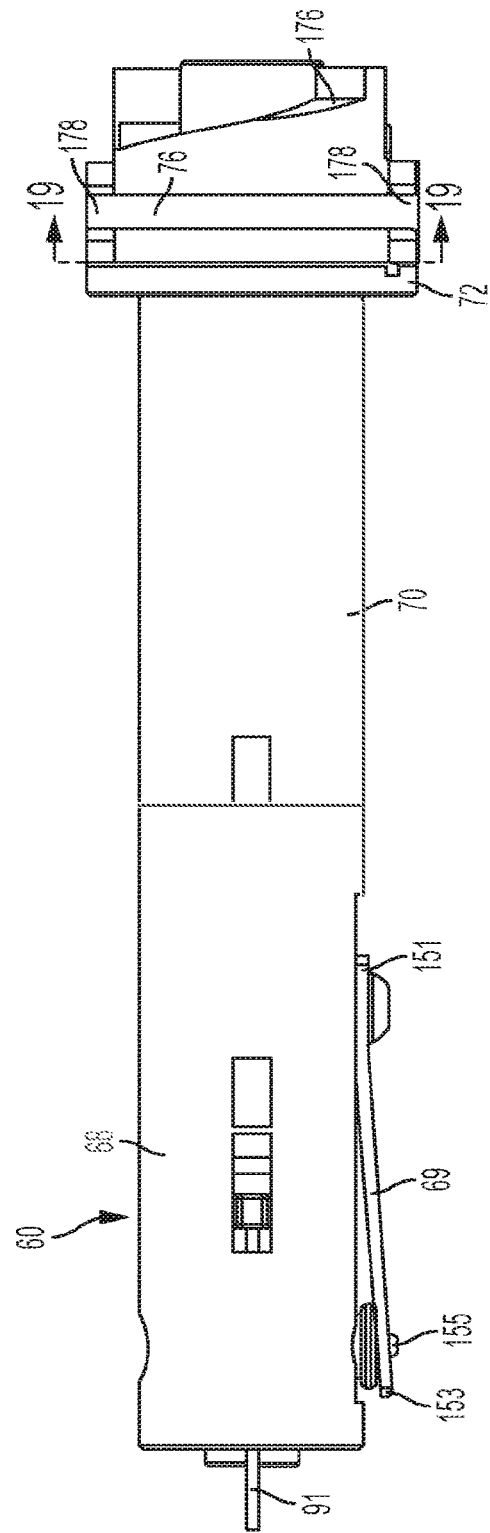
FIG. 19 is a perspective view of a propulsion cartridge in accordance with an embodiment of the present disclosure.

As illustrated in FIGS. 4, 17, and 19, the propulsion cartridge 60 may include a propulsion rod 62, a propulsion spring 66 positioned about at least a portion of the propulsion rod 62, a first housing 68, a second housing 70, and the trigger pin 67. The propulsion cartridge 60 may be removably coupled to the base assembly 10. For example, the illustrated embodiment of FIG. 2 shows that a "C" ring 77 may be used to removably couple the propulsion cartridge 60 to the base assembly 10. In particular, the "C" ring 77 may be positioned between the propulsion cartridge 60 and the base assembly 10 to frictionally couple (e.g., by a compression fitting) the propulsion cartridge 60 and the base assembly 10. In other embodiments, the propulsion cartridge 60 may be removably coupled to the base assembly 10 by fasteners, catches, or by other means as known in the art. In other embodiments, the "C" ring 77 may be omitted.

The propulsion spring 66 has a pressure profile associated therewith to effectuate the jet injection, as described in greater detail below. The propulsion spring 66 may have a spring rate ranging from about 10 to about 50 lbs., from about 25 to about 45 lbs. and from about 30 lbs. to about 40 lbs. In particular, the spring rate of the propulsion spring 66 may be 35 lbs. (e.g., 35 pounds per inch).

While the propulsion cartridge 60 is illustrated as being a spring-based system, it is to be understood that the propulsion cartridge 60 may include a $CO_2$ based system, a compressed air based system, and the like.

The trigger pin 67 is generally tubular shaped and includes a body 150. The body 150 has a first portion 154, a second portion 156, a protrusion 155 extending from a bottom surface of the second portion 156, and a channel 152 extending at least partially therethrough. In the embodiment of FIG. 4, the outer diameter of the second portion 156 is greater than the outer diameter of the first portion 154. The trigger pin 67 is operably coupled to the trigger assembly 24 by the trigger post 27. Illustrated in FIG. 12, the trigger post 27 engages with the channel 152 of the trigger pin 67 via an aperture 182 in the first housing 68 of the propulsion cartridge 60. The channel 152 can be operably coupled to the trigger post 27 using any means known in the art. In particular, the trigger post 27 and channel 152 are threaded and are configured to be threadably coupled.

Illustrated in FIGS. 12 and 19, a leaf spring 69 is cantilevered and has a first end 151 and a second end 153. The second end 153 has an orifice 157 therethrough that is able to receive the protrusion 155 of the trigger pin 67. The first end 151 of the leaf spring 69 is fastened to the first housing 68 of the propulsion cartridge 60. The second end 153 of the leaf spring 69 is free-floating and is positioned adjacent the second portion of the trigger pin 67, opposite the housing aperture 182, to urge the trigger pin 67 along the second axis B toward a locked position, as described in greater detail below. In particular, the trigger pin 67 is configured to slide in a direction parallel to the second axis B. In one embodiment, the trigger pin 67 may slide in a direction coaxial with the second axis B. Therefore, when depressed, the trigger assembly 24, through the trigger post 27, actuates the trigger pin 67 in a direction opposite that of the urging direction by the leaf spring 69. In some embodiments, the protrusion of the trigger pin 67 operably engages a microswitch 128 to begin an EP timing sequence, as described in greater detail below.

A lower end 73 of the second housing 70 of the propulsion cartridge 60 is configured to receive a portion 158 of the first housing 68 of the propulsion cartridge 60 such that the first and second housings 68, 70 are axially aligned and further define a third axis C. In the illustrated embodiment of FIG. 1, the third axis C is coaxial with the first axis A In other embodiments, the third axis C may be parallel to, but not coaxial with, the first axis A When coupled together, the housings 68, 70 define a substantially cylindrical interior having a passage 160 configured for the propulsion rod 62 to extend therethrough. At an upper end 71, the second housing 70 includes a flange 72 and an extension 74 of a smaller diameter than the flange 72. The flange 72 is shaped to fit within a recess 162 at the upper end 12 of the housing 16 for a firm fitting between the propulsion cartridge 60 and the housing 16. The extension 74 includes a plurality of slots 164 that operably engage the propulsion rod 62, as explained in further detail below. The second housing 70 may also include an interior lip 75 for providing a first seat for a first end 168 of the propulsion spring 66, as illustrated in FIG. 9.

Figure 7A:
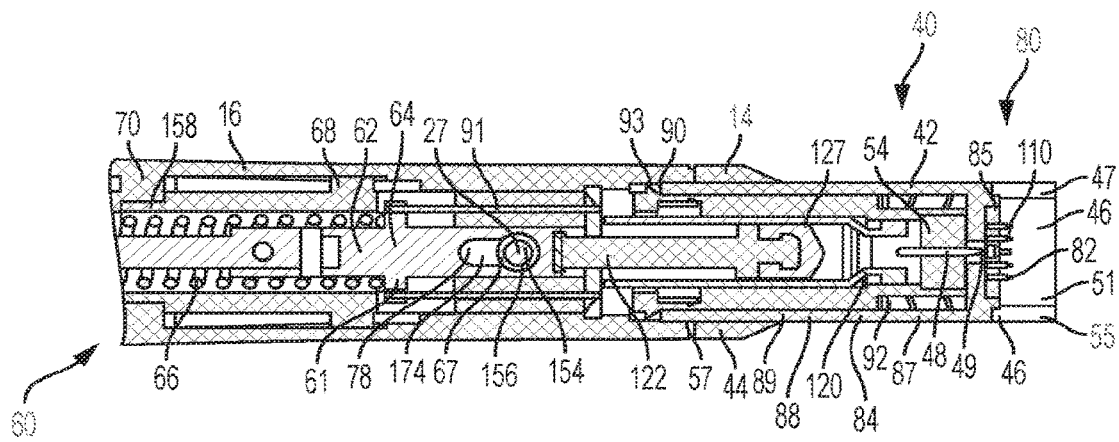
FIGS. 7A and 7B are cross-sectional top perspective views of an array trigger mechanism in accordance with embodiments of the present disclosure.
Figure 7B:
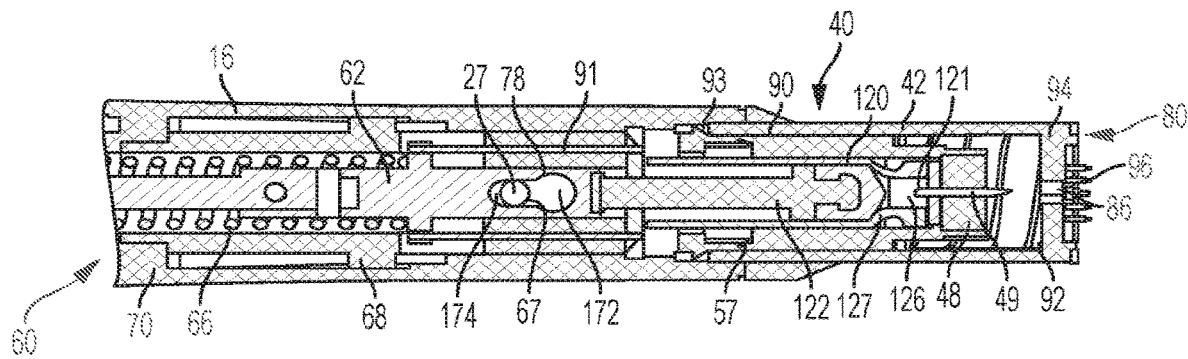

The propulsion rod 62 includes a lower end 64 and an upper end 65. The upper end 65 of the propulsion rod 62 includes a pin 63 such that the propulsion rod 62 and the pin 63 have a "T" configuration. The pin 63 is configured to fit within the slots 164 of the extension 74 of the second housing 70 to prevent rotation of the propulsion rod 62, as explained in further detail below. The lower end 64 includes a lip 61 and a slot 78 which extends through the propulsion rod 62 such that the trigger pin 67 may extend therethrough. The lip 61 provides a second seat for a second end 170 of the propulsion spring 66. The slot 78, similar to the trigger pin 67, includes two sections that vary in diameter. Specifically, a large section 172 of the slot 78 has a diameter that is slightly larger than the outer diameter of the second portion 156 of the trigger pin 67 so that the second portion 156 of the trigger pin 67 is able to fit within the large section 172 of the slot 78. Likewise, a small section 174 of the slot 78 has a diameter that is slightly larger than the outer diameter of the first portion 154 of the trigger pin 67 so that the first portion 154 of the trigger pin 67 is able to fit within the small section 174 of the slot 78. As illustrated in FIG. 7B, the second portion 156 of the trigger pin 67 has an outer diameter too large to fit within the small section 174 of the slot 78.

Figure 18:
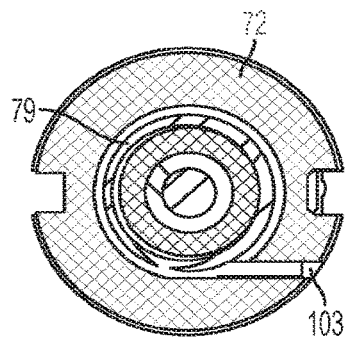
FIG. 18 is a cross sectional rear view of the line "A" of FIG. 17.
Figure 20:
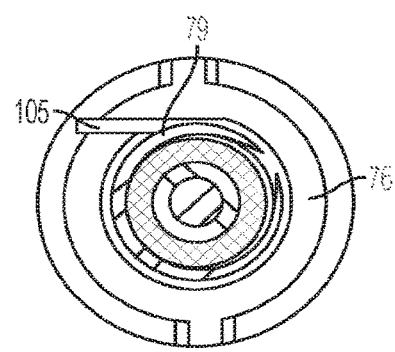
FIG. 20 is a cross sectional front view of the line "B" of FIG. 19.
Figure 21A:
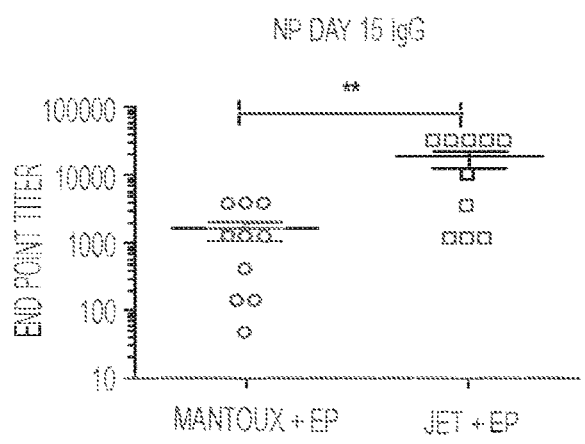
FIGS. 21A and 21B depict nucleoprotein IgG end point titers at days 15 and 22 measured by ELISA Bars between groups represent a statistical difference of $p<0.01$ ** or non-significant (ns) as measured by at-test.
Figure 21B:
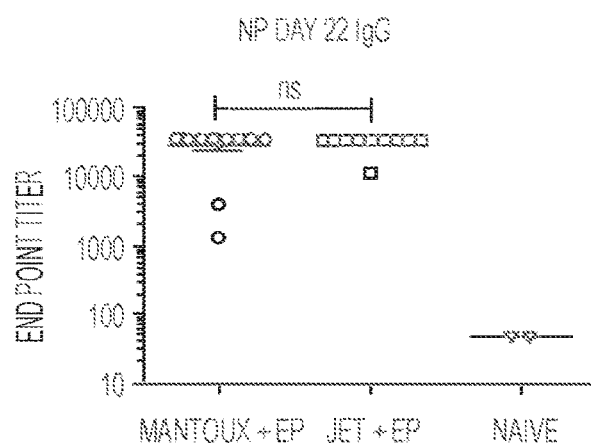
Figure 22A:
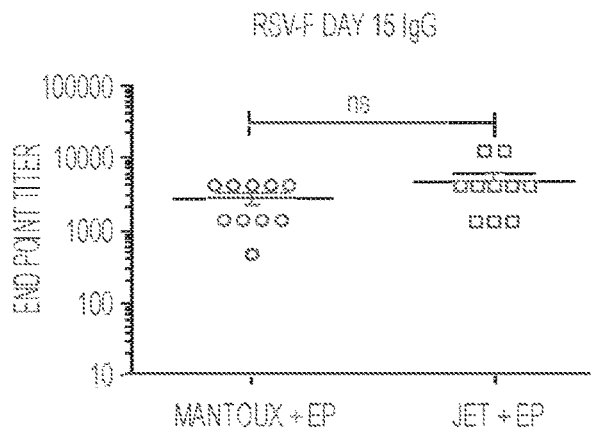
FIGS. 22A and 22B depict RSV-F antigen IgG end point titers at days 15 and 22 measured by ELISA Bars between groups represent a statistical difference of $p<0.001$ (***) or non-significant (ns) as measured by Student's t-test.
Figure 22B:
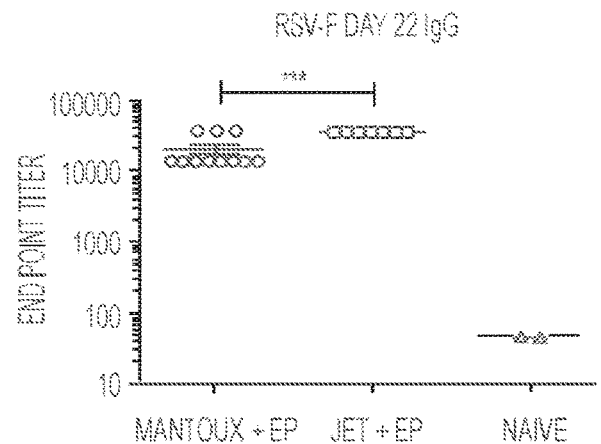
Figure 23A:
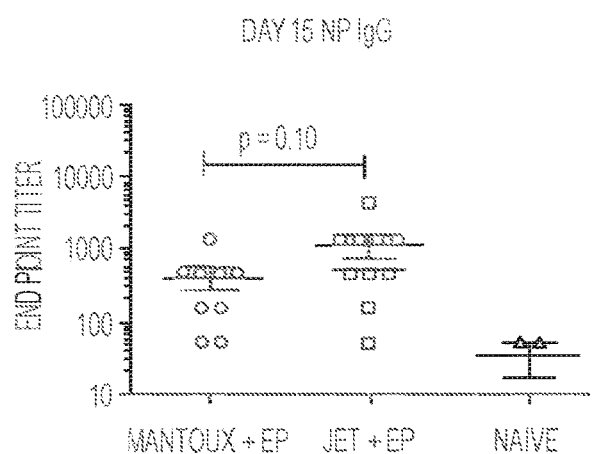
FIGS. 23A and 23B depict nucleoprotein IgG end point titers at days 15 and 22 measured by ELISA Bars between groups represent a statistical difference of $p<0.01$ ** or non-significant (ns) as measured by at-test.
Figure 23B:
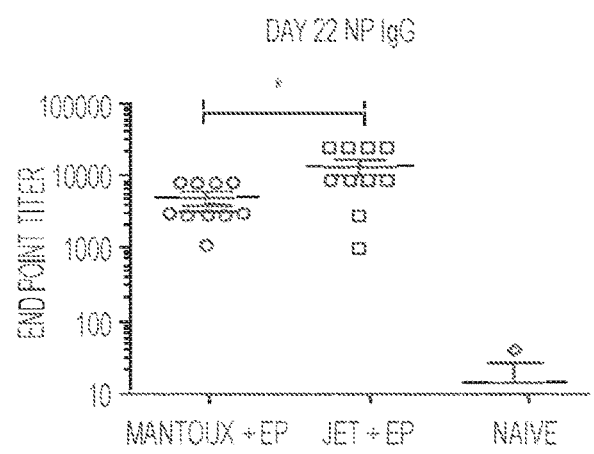
Figures 24A, 24B:
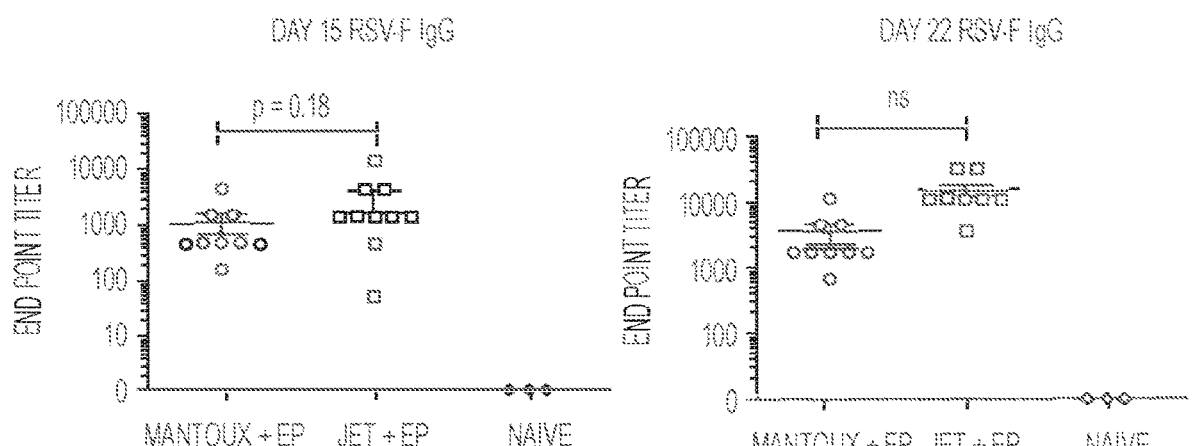
FIGS. 24A and 24B depict RSV-F antigen IgG end point titers at days 15 and 22 measured by ELISA Bars between groups represent a statistical difference of $p<0.001$ (***) or non-significant (ns) as measured by Student's t-test.

The propulsion cartridge 60 also includes an arming cam 76 and a return spring 79. The arming cam 76 and the return spring 79 are each configured to be positioned over the extension 74 of the second housing 70. The return spring 79 may operably engage the rotational knob 30 such that the return spring 79 urges the rotational knob 30 in a clockwise or counterclockwise direction, as explained in greater detail below. The arming cam 76 includes helical ramped surfaces 176 configured to engage the pin 63 of the propulsion rod 62. The arming cam 76 may also include at least two extensions 178 configured to engage the rotational knob 30, as illustrated in FIG. 9. The arming cam 76 may include a groove 105 for accepting an end of the return spring 79, illustrated in FIG. 20. The surface of the flange 72 facing the arming cam 76 may also have a groove 103 for accepting an opposite end of the return spring 79, as illustrated in FIG. 18. The grooves of the arming cam 76 and the flange 72 allow the return spring 79 to return the arming cam 76, and consequently the rotational knob 30, to its resting position.

Figure 9:
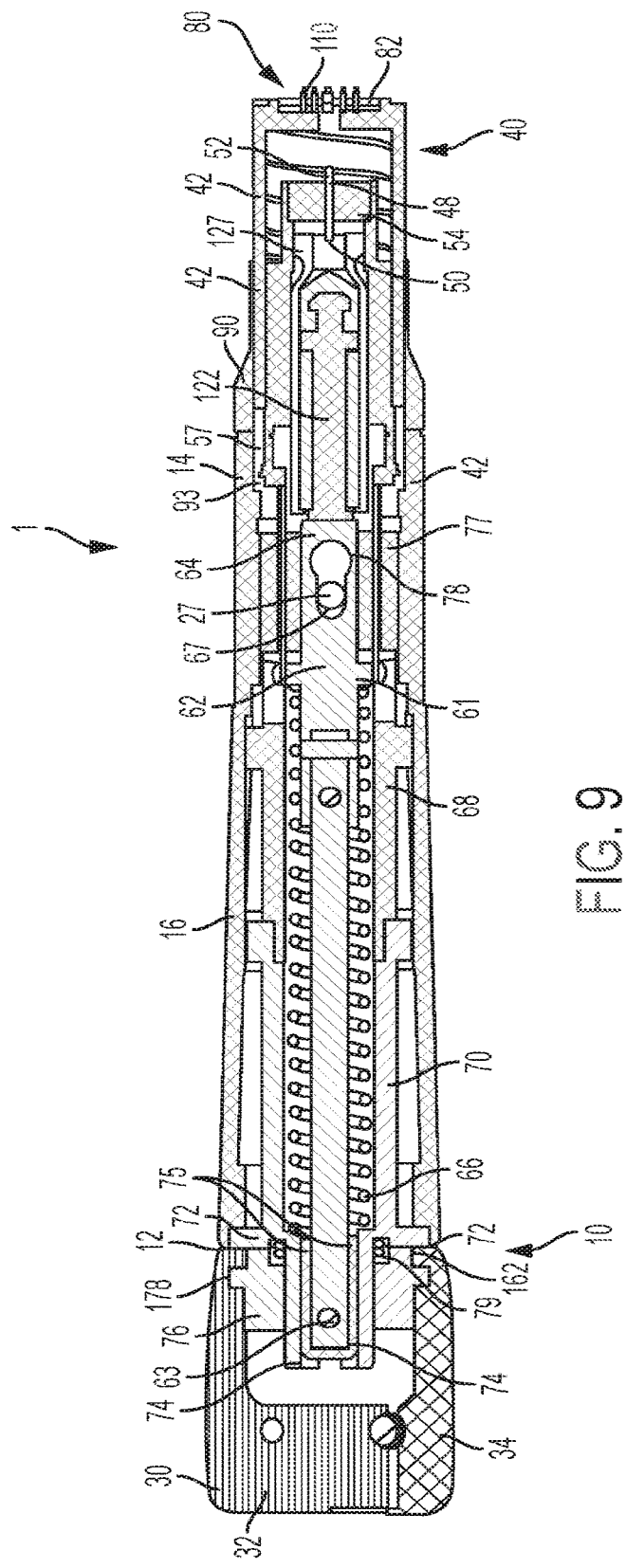
FIG. 9 is a top cross-sectional view of a jet injection and EP combination device in accordance with an embodiment of the present disclosure.
Figure 14:
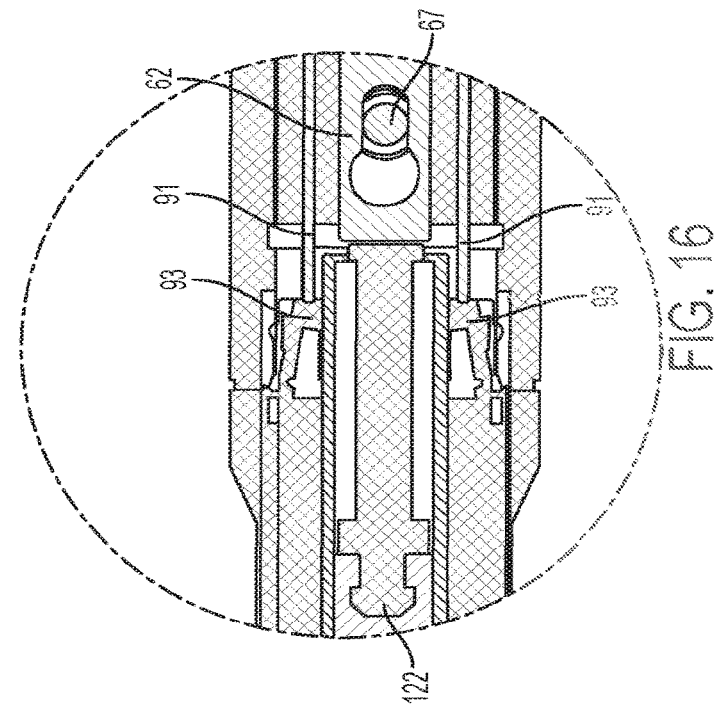
FIG. 14 is a close-up view of the circle "A" of FIG. 13.
Figure 16:
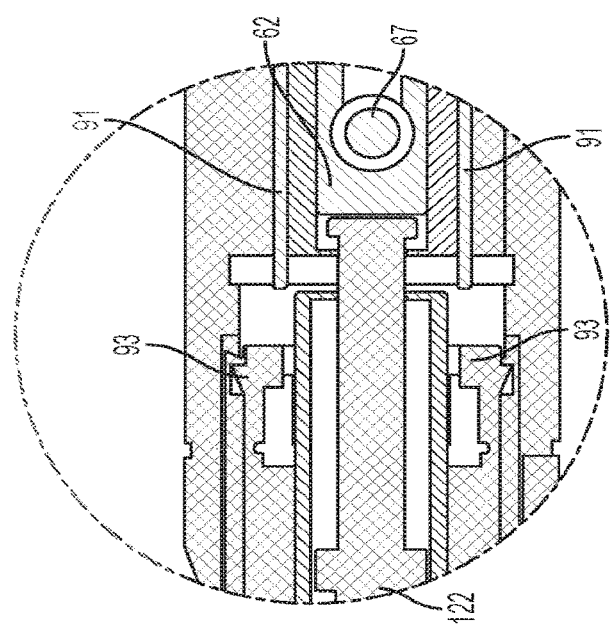
FIG. 16 is a close-up view of the circle "B" of FIG. 15.

As assembled, the propulsion cartridge 60 is positioned within the housing 16, as illustrated in FIG. 9. The first housing 68 and the second housing 70 are coupled to provide the passage 160 through which the propulsion rod 62 is configured to extend. The propulsion spring 66 is positioned about the propulsion rod 62, between the slot 78 and the pin 63. In particular, the first end 168 of the propulsion spring 66 is positioned against the interior lip 75 of the first housing 68 and the second end 170 of the propulsion spring 66 is positioned against the lip 61 of the propulsion rod 62. The trigger pin 67 is positioned in the slot 78 such that the propulsion rod 62 is capable of moving in a direction parallel to the first axis A In particular, the propulsion rod 62 is generally capable of moving between a relaxed position, as illustrated in FIGS. 7B and 16, and a locked or armed position, as illustrated in FIGS. 7A and 14.

The propulsion spring 66 provides a force which urges the propulsion rod 62 toward the lower end 14 of the base assembly 10 or relaxed position so that the large section 172 of the slot 78 is aligned with the trigger pin 67 in a direction parallel with the second axis B. In the relaxed position, illustrated in FIG. 7B, the first portion 154 of the trigger pin 67 is positioned within the slot 78. As briefly described above, the leaf spring 69 provides a force which urges the trigger pin 67 along the axis B such that when the large section 172 of the slot 78 is presented to the trigger pin 67, the second portion 156 of the trigger pin 67 moves into the slot 78. As the second portion 156 of the trigger pin 67 has an outer diameter larger than the small section 174 of the slot 78, the propulsion rod 62 is locked in place by the urging force of the propulsion spring 66. In this locked position, illustrated in FIG. 7A, the propulsion spring 66 is compressed and is configured to provide an injection force. When the trigger assembly 24 is actuated to its second, depressed position, the trigger pin 67 is displaced in a direction opposite to the direction of the leaf spring 69 force. The displacement of the trigger pin 67 moves the second portion 156 so that the second portion 156 is no longer positioned within the slot 78 and first portion 154 moves into the slot 78. The outer diameter of the first portion 154 of the trigger pin 67 is smaller than both the large and the small section 172, 174 of the slot 78 so that movement of the propulsion rod 62 is not restricted. This allows for the propulsion spring 66 to relax and move the propulsion rod 62 forward to the relaxed position to provide the injection force.

Furthermore, the rotational knob 30 is coupled to the extensions 178 of the arming cam 76. Accordingly, when the rotational knob 30 is rotated, the arming cam 76 is also rotated. The arming cam 76 allows for the transformation of the rotational force generated by the rotational knob 30 to collapse/compress the propulsion spring 66. The arming cam 76 and the return spring 79 are both positioned about the extension 74 of the second housing 70, between the pin 63 and the flange 72. The helical ramped surfaces 176 of the arming cam 76 are positioned against the pin 63, which is positioned within the slots 164 of the extension 74. Therefore, when the arming cam 76 is rotated by the rotational knob 30, the helical ramped surfaces 176 force the pin 63 in a direction parallel to the axis A away from the first housing 68 (e.g., to the left with respect to FIG. 9). However, the propulsion rod 62 does not substantially rotate with the arming cam 76 and the rotational knob 30 because the pin 63 is positioned within the slots 164 of the extension 74. The propulsion rod 62, being coupled to the pin 63, begins to move away from the trigger pin 67 and the propulsion spring 66 begins to compress against the interior lip 75. When the rotational knob 30 has been rotated about 180 degrees, the propulsion rod 62 has been moved far enough such that the large section 172 of the slot 78 is presented to the trigger pin 67, allowing the second portion 156 of the trigger pin 67 to move into the slot 78, as explained above. The return spring 79 may urge the rotational knob 30 back toward its original (e.g., at-rest) position after the propulsion rod 62 has been moved to the locked position. In other embodiments, the rotational knob 30 may need to be rotated more or less than 180 degrees to move the propulsion rod 62 from the relaxed position to the locked position.

As illustrated in FIGS. 1 and 3, the jet injection module 40 includes an injection housing 42 having openings 45, 47 at both an upper end 44 and a lower end 46, respectively. The lower end 46 defines an edge 43 that surrounds the opening 47. The upper end 44 is configured to receive a portion of a cartridge 120 and may be removably coupled with the housing 16 at the lower end 14 of the base assembly 10. As illustrated in FIG. 1, the jet injection module 40 may include detents 41 for coupling to a groove 39 positioned in the cavity 18 at the lower end 14 of the housing 16. The detents 41 and groove 39 are configured to allow a user to quickly remove and attach the jet injection module 40 from the base assembly 10. Furthermore, the injection housing 42 may include various sidewalls, ridges, detents, and the like to support the cartridge 120 when positioned therein. More specifically, the injection housing 42 may include components to help absorb or minimize the pressure forces experienced by the cartridge 120.

Figure 5:
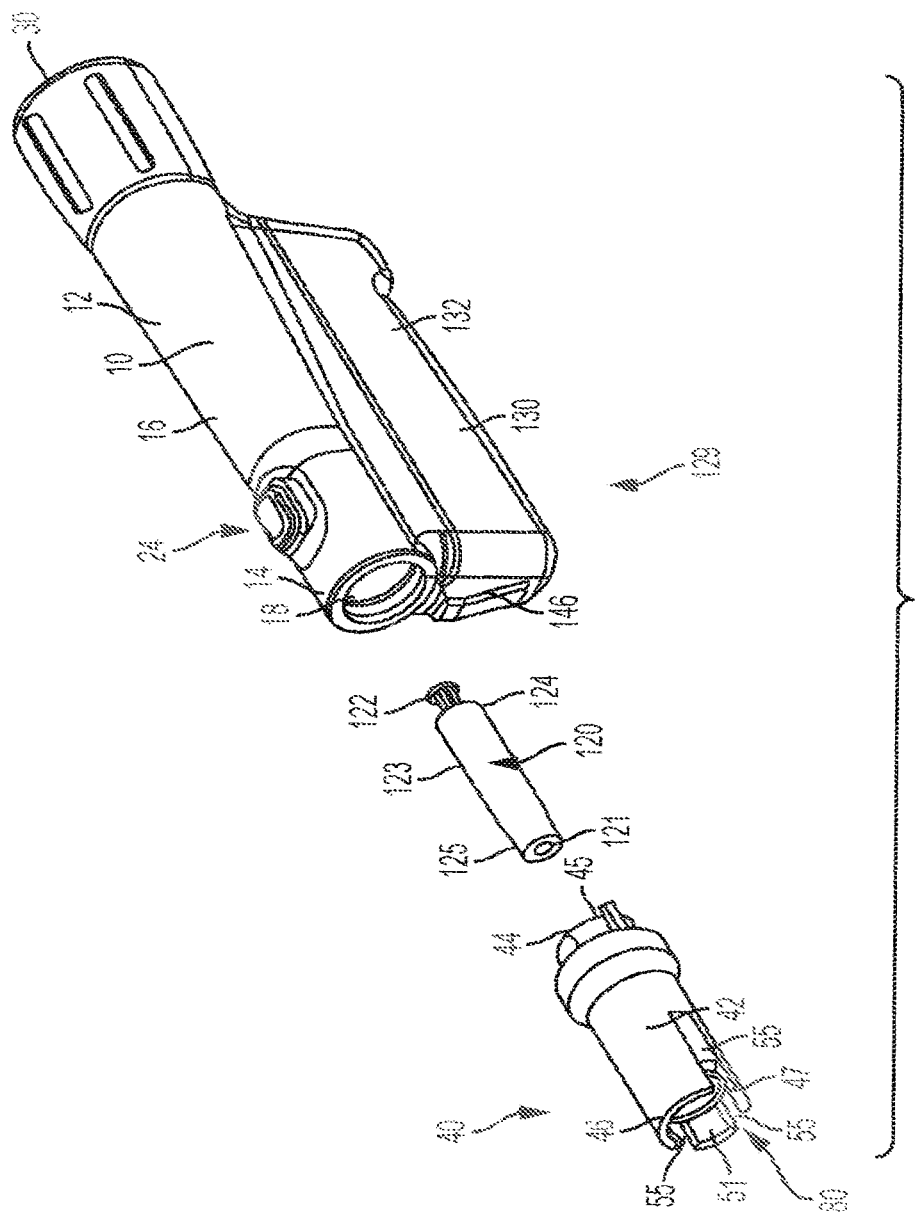
FIG. 5 is an exploded side view of a jet injection and electroporation (EP) delivery device in accordance with an embodiment of the present disclosure as well as a cartridge.
Figure 6:
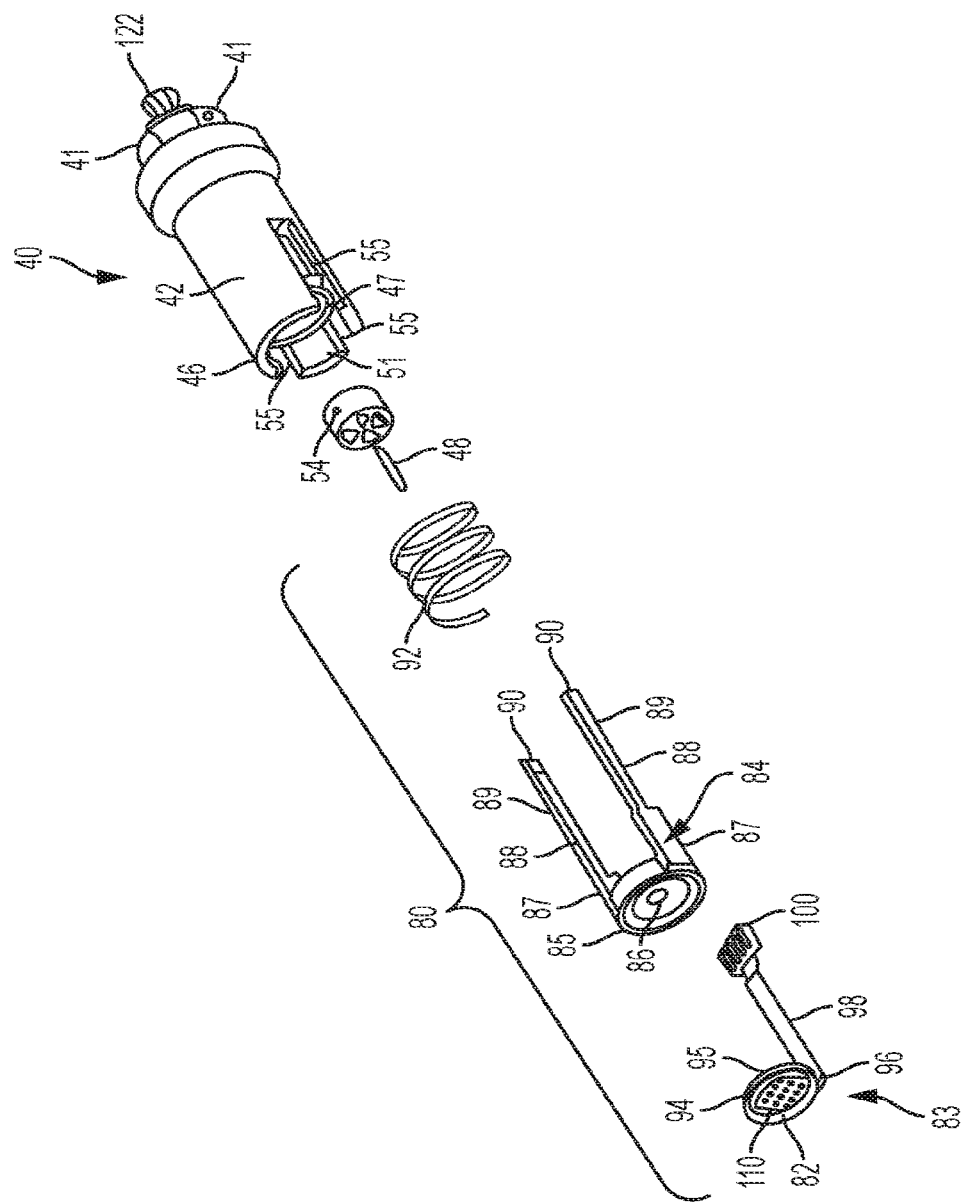
FIG. 6 is an exploded side view of a jet injection module and EP array assembly combination in accordance with an embodiment of the present disclosure.

As illustrated in FIGS. 5 and 6, the housing 42 may also include outer recesses 55 extending from the lower end 46 to a point on the housing 42, as illustrated in FIGS. 5 and 6. The housing 42 may further include interior recesses 57 which extend from the outer recesses 55. As illustrated in FIGS. 7A. 7B, and 13-16, the interior recesses 57 may be generally smaller than the outer recesses 55 and include release pins 91 and latch detents 93 at each of their respective ends, as explained in further detail below.

The jet injection module 40 generally includes a nozzle 48 and a mounting boss 54 configured to accept the nozzle 48. The mounting boss 54 may, for example, be a spider clamp. A volume 51 defined by the injection housing 42 is configured to removably receive the mounting boss 54 therein. The mounting boss 54 may be frictionally coupled (e.g., by a compression fitting) to the injection housing 42 such that the mounting boss 54 is substantially held in place during operation of the system 1, as explained in further detail below. In other embodiments, the mounting boss 54 may be removably coupled to the injection housing 42 by fasteners, catches, or by other means as known in the art.

The nozzle 48 has a proximal end 50, a distal end 52, and a conduit 53 extending therebetween such that the proximal end 50 and the distal end 52 each includes an opening of the conduit 53. The proximal end 50 may be beveled so as to be capable of penetrating a septum 121 of the cartridge 120, when the cartridge 120 is inserted in the jet injection module 40. The distal end 52 includes a nozzle tip 49 configured to deliver a jet injection to a patient, as described in greater detail below. The nozzle 48 may be removably positioned within the mounting boss 54 such that the nozzle 48 extends axially with the system 1 (e.g., a longitudinal axis of the nozzle 48 extends parallel with the first axis A). The diameter of the openings and the conduit 53 may be designed to any configuration necessary to meet the need of the jet injection cycle to be employed. In one embodiment, the diameter may be about 0.05 mm to about 0.064 mm and may deliver a pressure of about 10.000 to about 30.000 Psi to the skin surface, as explained in greater detail below.

The nozzle 48 is removably coupled to the mounting boss, which is removably coupled to the injection housing 42 so that it can be interchanged with nozzles of varying configurations. The nozzle 48 can have various tapering and tip 49 configurations, thereby allowing a jet stream to be applied to a patient's skin surface in a number of differing patterns. The nozzle 48 can also have various internal funneling configurations capable of allowing for the jet stream to have a laminar flow or a turbulent flow. Accordingly, changing the nozzle tip 49 may enhance transfection by including things such as, but not limited to, multiple orifice outlets configured to increase distribution of the liquid and coverage of electroporation.

The distance between the surface of the subject's skin and the distal end 52 of nozzle 48 can vary in according to a number of factors including but not limited to, the viscosity of the agent, the spring rate of the propulsion spring 66, and the diameter of the nozzle tip 49. For example, the nozzle tip 49 can be about 0.5 cm to about 2.0 cm above the surface of the subject's skin.

The base assembly 10, the jet injection module 40, and the propulsion cartridge may be made of materials known in the art including, but not limited to, plastic (e.g., polycarbonate), ceramic, and stainless steel or other metals.

As illustrated in FIGS. 5 and 6, the system 1 can further include an EP array assembly 80. The EP array assembly 80 generally includes an array 82 having at least two needle electrodes 110, a flex circuit 83, a mounting support slide 84, and an array spring 92. The EP array assembly 80 may be removably coupled to and positioned within the volume 51 at the lower end 46 of the injection housing 42, as explained in greater detail below.

As illustrated in FIGS. 10A-10F, the flex circuit 83 includes a base plate 94 having a first orifice 96 at its center, a circuit extension 98, and electrical contacts 100. The base plate 94 is configured to receive and support the array 82. The array 82 is positioned on the base plate 94 such that the electrodes 100 extend in a first direction from the base plate 94 (e.g., to the left with respect to FIGS. 10D-10F). The circuit extension 98 is configured to electrically couple the array 82 and the electrical contacts 100. The circuit extension 98 projects from a side 95 of the base plate 94 in a direction that is generally perpendicular to the first direction (e.g., up with respect to FIGS. 10D-10F) and continues to extend in a second direction from the base plate 94. The second direction is generally opposite the first direction (e.g., to the right with respect to FIGS. 10D-10F).

The mounting support slide 84 includes a depression 85 configured to receive at least a portion of the base plate 94. In one embodiment, the depression 85 may be about half of the width of the base plate 94 so that, when assembled, the circuit extension 98 projects from the base plate 94 from outside of the depression 85. In other embodiments, the depression 85 may include a channel (not illustrated) extending to the perimeter of the base plate 94, which is shaped so that the circuit extension 98 may be positioned therein. In yet other embodiments, the mounting support slide 84 may not include a depression 85 and aligns the base plate 94 on the mounting support slide 84 by other methods.

The mounting support slide 84 further includes a second orifice 86 positioned in the center of the depression 85 and two outrigger extensions 88. The base plate 94 is positioned on the mounting support slide 84 so that the first orifice 96 and the second orifice 86 are generally aligned. As illustrated in FIG. 6, the outrigger extensions 88 are positioned on opposite sides of the mounting support slide 84. The outrigger extensions 88 each include a wide portion 87 which has a height that is generally equal to the height of the outer recesses 55 and a narrow portion 89 which has a height that is generally equal to the height of the interior recesses 57. Each outrigger extension 88 includes a latch 90 at the end of the narrow portion 89 that is configured to couple to the latch detents 93 positioned at the end of the interior recesses 57.

As assembled, the EP array assembly 80 is configured to move axially from a first (e.g., retracted) position to a second (e.g., extended) position within the volume 51 of the injection housing 42. In the first position illustrated in FIG. 7A, the EP array assembly 80 is retracted within the injection housing 42. In the second position illustrated in FIG. 7B, the EP array assembly 80 is moved distally (e.g., to the right with respect to FIGS. 7A, 7B) from the first position so that the array 82 may come into contact with a subject's skin region for electroporation, as explained in greater detail below.

Figure 11:
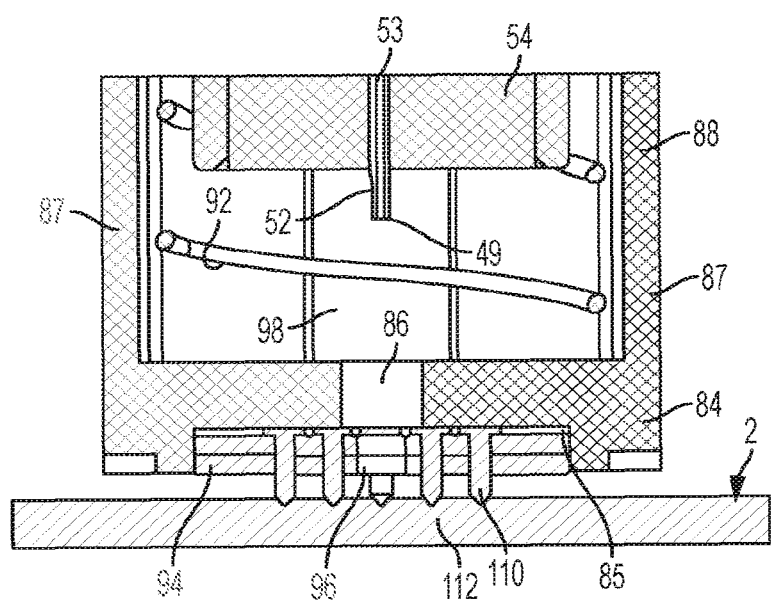
FIG. 11 depicts a cross sectional side view of different grind angles on array electrodes penetrating the skin surface during an EP treatment in accordance with an embodiment of the present disclosure.
Figure 13:
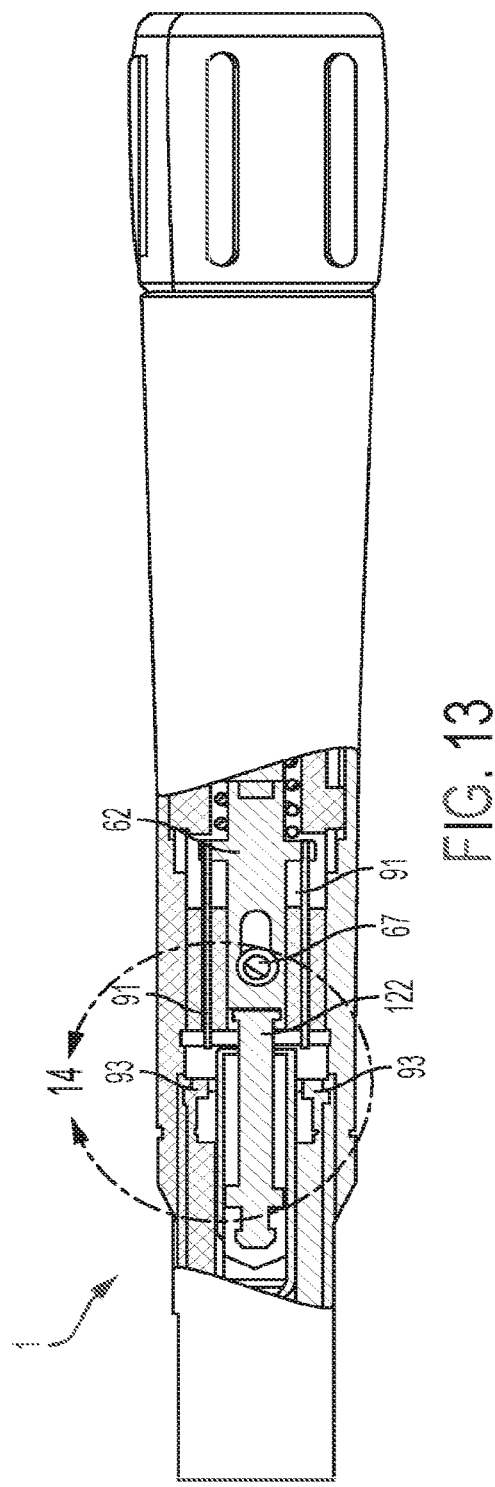
FIG. 13 is a partial cross-sectional view of a jet injection and EP combination device in accordance with an embodiment of the present disclosure and depicts a plunger in an assembled position.
Figure 15:
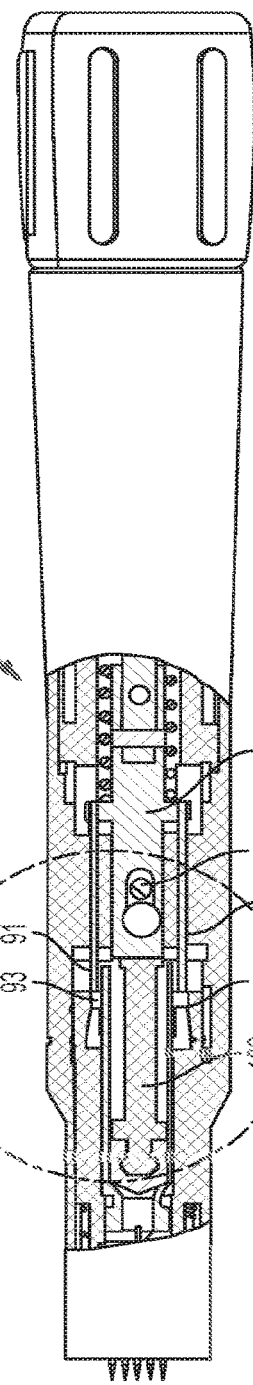
FIG. 15 is a partial cross-sectional view of a jet injection and EP combination device in accordance with an embodiment of the present disclosure and depicts a plunger in a depressed position

In particular, the array spring 92 is inserted into the volume 51 of the injection housing 42 so that at least a portion of the array spring 92 is positioned about mounting boss 54, as illustrated in FIG. 11. The flex circuit 83 is coupled to the mounting support slide 84 so that the first orifice 96 and the second orifice 86 are aligned. The flex circuit 83 and mounting support slide 84 assembly may then be positioned within the volume 51 of the injection housing 42. Specifically, as illustrated in FIG. 6, the wide portions 87 of the outrigger extensions 88 may be positioned in the interior recesses 57 of the injection housing 42 and the narrow portions 89 may be positioned in the outer recesses 55 to orient the mounting support slide 84 so that the latches 90 of the outrigger extensions 88 may couple to the latch detents 93. As illustrated in FIG. 7A, the array spring 92 may be compressed by the mounting support slide 84, after insertion of the outrigger extensions 88 into the recesses 55, 57, thereby readying the support slide 84 to provide for the array 82 deployment force. The latches 90 maintain the EP array assembly 80 in the retracted position (i.e., the array spring 92 is compressed) by the coupling to the latch detents 93, as illustrated by FIGS. 13 and 14. The latch detents 93 may be coupled to the trigger assembly 24 such that when the trigger assembly 24 is actuated, the latch detents 93 release the latches 90 through a pair of release pins 91. The decoupling between the latches 90 and the latch detents 93 allows the array spring 92 to relax and force the mounting support slide 84, and therefore the flex circuit 83, outward (e.g., to the right with respect to FIG. 9) to provide the array 82 deployment force for electroporation, as illustrated by FIGS. 15 and 16. The release pins 91 may be attached to the propulsion rod 62, as illustrated in FIGS. 7A, 7B, and 13-15. When the trigger assembly 24 is actuated, the release pins 91 move forward with the propulsion rod 62 and engage the latch detents 93, as illustrated in FIG. 13. The release pins 91 push the latch detents 93, forcing the latch detents 93 inward (e.g., toward the first axis A), allowing the array spring 92 to expand.

The deployment force of the mounting support slide 84 and the flex circuit 83 may be determined by the spring rate of the array spring 92. The array spring 92 may have a spring rate ranging from about 1 lb. to about 20 lbs., from about 2 lbs to about 10 lbs. from about 4 lbs. to about 6 lbs. and may be 5 lbs (e.g., 5 pounds per inch). The array spring 92 may be changed between deliveries in order to differ between different spring rates depending on the agent and dosage to be delivered. In other embodiments, the system 1 may also include a sensor (not illustrated) for determining the force applied to the EP array assembly 80 when positioned on a subject by a user. The sensor may be configured to determine the amount of force that is being applied by the user to the system 1 on the subject's skin so that the user does not apply too large or too little force. An auditory and/or visual signal (e.g., by an annunciator or an illuminated LED) may indicate if the user is using too large or too little force. Alternatively, the auditory and/or visual signal may indicate when the user is using a correct amount of force.

After actuation (e.g., the array spring 92 forcing the mounting support slide 84 forward), the EP array assembly 80 may be manually rearmed or re-cocked for use by pushing the EP array assembly 80 back into the retracted position. In other embodiments, the jet injection module 40 may be disposable, where the module 40 is ready for use such that the EP array assembly 80 is in the locked position prior to the module 40 being operably coupled to the base assembly 10.

Figure 10A:
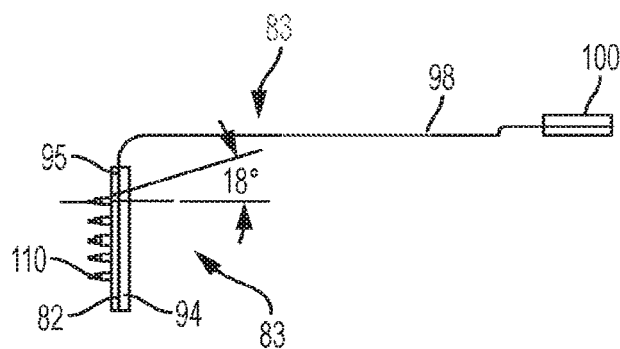
FIGS. 10A-10C depict a side view of grind angles on array electrodes in accordance with embodiments of the present disclosure.
Figure 10B:
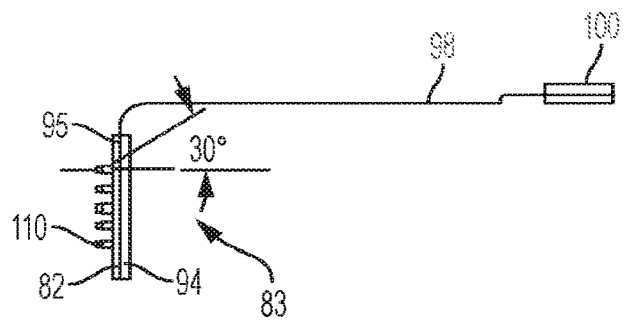
Figure 10C:
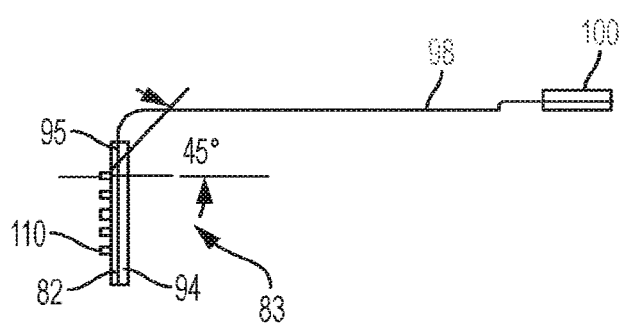
Figure 10D:
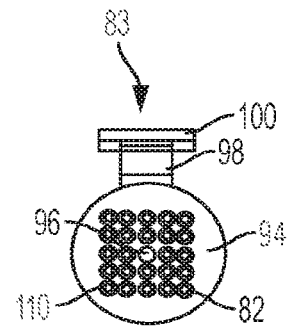
FIGS. 10D-10F depict a front view of the array electrodes of FIG. 10A-10C.
Figure 10E:
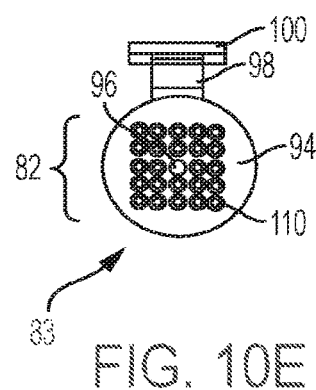
Figure 10F:
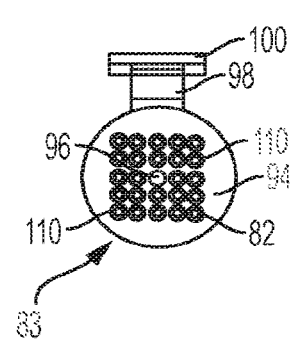

As briefly mentioned above, the flex circuit 83 includes electrical contacts 100 to form an electrical connection with a corresponding electrode 110 of the array 82. In the illustrated embodiment of FIG. 6, the array 82 includes two electrical contacts 100 each coupling with a respective electrode 110. However, in alternative embodiments, more or fewer electrical contacts 100 may be present. For example, a set number of electrical contacts 100 may be present to permit the use of different size arrays (not illustrated), each having a different number of electrodes 110. For example, as illustrated in FIGS. 10D-10F, the array 82 may include a set of 24 electrodes 110 (e.g., a 5×5 electrode arrangement with the centermost electrode being omitted) and 24 electric contacts 100. In other embodiments, the electrodes 110 of array 82 can be spaced such that the centermost electrode does not need to be omitted.

The EP array assembly 80 is configured to orient the at least two electrodes 110 for electroporation of the patient. For example, when more than two electrodes 110 are used, the electrodes 110 are arranged to be evenly distributed over the array 82, or over the base plate 94 to which the electrodes 110 are attached, in square, circular, triangular, or other patterns. In another example, the needle electrodes 110 are arranged in a square-like arrangement with each adjacent electrode 110 spaced apart in approximately the same distance, except for the electrodes 110 on the edge of the square array 82. The array 82 may include at least two electrodes, 2×2 electrodes, 3×3 electrodes, 4×4 electrodes, 5×5 electrodes, 6×6 electrodes, 7×7 electrodes, 8×8 electrodes, 9×9 electrodes, 10×10 electrodes or greater. In particular, the array 82 may include 4×4 electrodes or 5×5 electrodes. Furthermore, each electrode 110 may be spaced apart from each adjacent needle electrode 110 at a distance of about 150 mm or less, from about 100 mm to about 1 mm, from about 50 mm to about 1 mm, from about 40 mm to about 1 mm, from about 30 mm to about 1 mm, from about 20 mm to about 1 mm, from about 10 mm to about 1 mm, from about 5 mm to about 1 mm, from about 5 mm to about 1 mm, from about 2.5 mm to about 1 mm, from about 2.5 mm to about 0.5 mm. In particular, the electrodes 110 may be spaced at a distance of about 2.5 mm to about 0.5 mm, or about 1.5 mm.

The array 82 may be formed using stamping or etching methods as known in the art. The electrodes 110 are configured to be minimally invasive and are configured to penetrate the epidermal tissue at depths not to exceed 1.0 mm, at depths ranging from about 0.01 mm to about 1.0 mm and particularly at depths ranging from about 0.01 mm to about 0.04 mm.

A variety of known electrodes 110 capable of delivering an electrical charge may be incorporated into an embodiment of the minimally invasive system 1 of the present disclosure. For example, the electrodes 110 may be substantially equivalent to a 25 gauge hypodermic needle. The at least two electrodes 110 of the array 82 extend away from the flex circuit base plate 94 to define a tip 112 having an angled edge 114 at a loading end of the electrode 110. As illustrated in FIGS. 10A-10C, a rake angle of the electrodes may be a defined angle between an axial centerline of the electrode 110 and the angled edge 114 of the electrode 110. For example, the rake angle may any angle between about 1 and about 90 degrees, between about 10 and about 45 degrees and can be about 10 degrees, about 18 degrees, about 30 degrees, or about 45 degrees. In particular, the rake angle may be 45 degrees from the centerline axis of the electrodes 110. As similarly stated above, the electrodes 110 are configured to penetrate layers of epidermis tissue between stratum corneum and basal layers, and are configured to deliver an electrical potential from a voltage generator to the epidermis tissue, as explained in further detail below. For example, the electrodes 110 may be of a size typically used in connection with minimally invasive intradermal electroporation.

While the illustrated device is illustrated with a plurality of electrodes 110 configured to penetrate layers of the epidermis tissue between stratum corneum and basal layers, it is also appreciated that the electrodes may include plate electrodes, microneedles, and both penetrating and non-penetrating needle electrodes configured to extend into various layers of tissue (for example into skeletal muscle tissue).

Each electrode 110 may also include a lead (not illustrated) extending from the electrode 110 opposite the tip 112. Each lead is in electrical communication with its corresponding electrode 110 and passes a current through the electrode 110 to produce an electrical interaction proximate the loading end. When the array 82 is installed, each electrode 110 of the array 82 is configured to engage and form an electrical connection with a corresponding electrical contact 100 of the flex circuit 83, as explained above.

As illustrated in FIG. 5, a pre-filled cartridge 120, briefly mentioned above, is configured to provide a disposable, one-time dose of a select agent. The disposable cartridge 120 is configured to be used with the injection module 40, as explained in further detail below. The cartridge 120 is substantially cylindrical in shape and is sized so as to be positioned between the nozzle 48 of the injection module 40 and the propulsion cartridge 60 within the housing 16 and the injection housing 42, as illustrated in FIGS. 7A. 7B. 9, and 15. The cartridge 120 includes a body 123. The body 123 defines a volume 126, is selectively sealed on a first end 124 by a plunger 122, and is selectively sealed on a second end 125 by the septum 121. As mentioned above, the septum 121 is configured to be punctured by the nozzle 48. It is to be understood that the body 123 of the cartridge may be formed from glass, plastic, or other materials.

The cartridge 120 also includes the plunger 122, mentioned above, positioned within the volume 126 and is moveable axially therewith between a start position, proximate the first end 124 of the body 123 and illustrated in FIGS. 7A. 15 and 16, and an end position, proximate the second end 125 of the body 123 and illustrated in FIGS. 7B, 13, and 14. The plunger 122 is shaped such that it forms a seal within the volume 126 of the body 123 at a plunger head 127. Movement of the plunger 122 from the start position toward the end position is configured to cause the volume 126 of the cartridge 120 to shrink, thereby forcing any fluid (e.g., the agent) contained therein out of the punctured septum 121.

Figure 8:
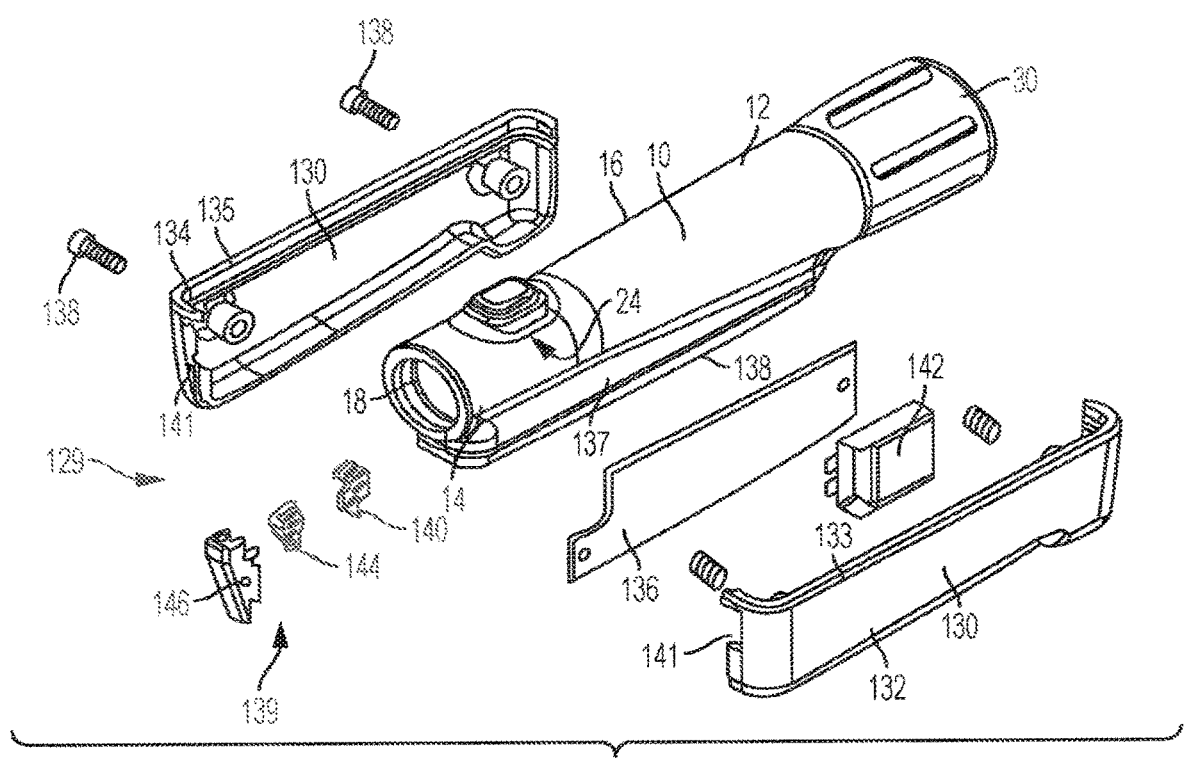
FIG. 8 is an exploded side view of an electroporation module in combination with a base assembly in accordance with an embodiment of the present disclosure.

The needle-free injection system 1 may also include an electrical system 129, illustrated in FIGS. 5, 8, and 12. The electrical system 129 generally includes an EP housing 130 and an electroporation assembly positioned within a volume defined by the EP housing 130. The electroporation assembly includes, among other things, a controller (not illustrated) having a printed circuit board ("PCB") 136, a waveform logger (not illustrated) in electrical communication with the controller, an electroporation pulse generator/module (not illustrated) in electrical communication with the controller and being configured to deliver an electric pulse, a power supply 142 in electrical communication with the electroporation pulse generator/module and configured to send an electrical charge to the pulse generator, and a plurality of electrical leads and contacts 140 configured to form an electrical connection with the electrical contacts 100 of the flex circuit 83.

The EP housing 130 generally includes a first case 132, a second case 134, and a plurality of fasteners 139 for coupling the first case 132 to the second case 134. As illustrated in FIG. 8, the housing 16 may include a lower projection 137 having a lip 138 configured to couple to the first case 132 and the second case 134. The first case 132 and the second case 134 each include a channel 133, 135 configured to accept the lip 138 of the lower projection 137. The channel 133, 135 is positioned at a top side of the first case 132 and the second case 134 such that when the first case 132 and the second case 134 are coupled to the housing 16, the EP housing 130 extends below the housing 16 (e.g., in a direction parallel to the second axis B). After the first case 132 and the second case 134 are positioned about the lip 138, the fasteners 139 may be inserted into openings 131 of the second case 134 and into threaded couplings (not illustrated) of the first case 132 to couple the first case 132 to the second case 134.

The EP housing 130 also generally includes a contact housing 146 and electrical contacts 140, which can be positioned between the first case 132 and the second case 134, as illustrated in FIG. 5. For example, the contact housing 146 may be positioned within a slot 141 defined by a space between the first case 132 and the second case 134.

In one embodiment, the electrical contacts 140 include a support 144. The electrical leads and contacts 140 are generally positioned throughout the system 1 to allow the various electrical components, as described above and below, to be in electrical/operable communication with one another. For example, the EP array assembly 80 and the electroporation pulse module which, as briefly mentioned above, is configured to deliver an electric pulse of selected voltage, current, and duration from the power supply 142 to the electrical contacts 140) and in turn to the electrodes 110 through the electrical contacts 100 of the mounting support slide 84.

The controller is configured to receive an input from the user by a user interface, instruct the pulse generator to deliver the pulse of energy to the desired tissue according to the input, and communicate data to the waveform logger according to the pulse of energy delivered, among other things. The controller may include a PCB 136, may be populated with a plurality of electrical and electronic components that provide power and operational control. In some embodiments, the PCB includes a processing unit (e.g., a microprocessor, a microcontroller, or another suitable programmable device), a memory, and a bus. The bus connects various components of the PCB including the memory to the processing unit. The memory includes, for example, a read-only memory ("ROM"), a random access memory ("RAM"), an electrically erasable programmable read-only memory ("EEPROM"), a flash memory, a hard disk, or another suitable magnetic, optical, physical, or electronic memory device. The processing unit is connected to the memory and executes software that is capable of being stored in the RAM (e.g., during execution), the ROM (e.g., on a generally permanent basis), or another non-transitory computer readable medium such as another memory or a disc. Additionally or alternatively, the memory is included in the processing unit. The controller also includes an input/output ("I/O") unit that includes routines for transferring information between components within the controller and other components of the system 1. The controller is also in electrical communication with a microswitch 128, briefly mentioned above, in electrical communication with the PCB, which provides a master enable signal to initiate a timing sequence to provide a delay between initiation of jet injection and electroporation. For example, the delay between the initiation of jet injection and electroporation may be about 100 microseconds. In other embodiments, the delay may be between 0 seconds and 2 milliseconds. The microswitch 128 also generates the timed sequence firing of electric pulse(s) through the EP array assembly 80, as explained in further detail below. The microswitch 128 is activated by depressing the push button 26 of the trigger assembly 24, explained in greater detail below and illustrated in FIG. 12.

Software included in some implementations of the system 1 is stored in the memory of the controller. The software includes, for example, firmware, one or more applications, program data, one or more program modules, and other executable instructions. The controller is configured to retrieve from memory and execute, among other things, instructions related to the control processes and methods described above and below. In some embodiments, the controller includes additional, fewer, or different components.

The PCB 136 also includes, among other components, a plurality of additional passive and active components such as resistors, capacitors, inductors, integrated circuits, and amplifiers. These components are arranged and connected to provide a plurality of electrical functions to the PCB 136 including, among other things, filtering, signal conditioning, or voltage regulation. For descriptive purposes, the PCB 136 and the electrical components populated on the PCB 136 are collectively referred to as the controller.

The system 1 may also be in communication, wirelessly or by other methods as known in the art, with a user interface, briefly mentioned above, to provide usage or status information to the user. The user interface can include, for example, a mobile tablet, a base station/stand, or another type of display. The present disclosure can also include annunciators including but not limited to, for example, a speaker (not illustrated) and LED's (not illustrated) for communication with the user regarding charging status of the battery and other information.

The system 1 may be paired with an external base station/stand (not illustrated) that is configured to be in communication with embodiments of the system 1 to provide the user with all the informational input advantages of a large, touchscreen interface (i.e., via base station) while still maintaining the flexibility and mobility of an untethered hand-held device (e.g., the needle-free injection system 1). On the base station, the user may be given multiple options for information input, including by typing (on the touchscreen display), or by downloading the information to a flash drive. The base station may also include a step-by-step graphic user interface that simplifies manual data entry. Still further, the base station may include a screen for displaying another graphic user interface that provides, among other things, step-by-step instructions in real-time as the procedure is occurring (i.e., real-time information). In addition to visual aids, the system 1 and the base station may include a high fidelity sound system consisting of a CODEC and a speaker to permit complex audio instructions (e.g., more than simple beeps) to be provided to the user.

The power supply 142 supplies a nominal AC or DC voltage to the base assembly. The power supply 142 may also be configured to supply lower voltages to operate circuits and components within the base assembly 10. In some implementations, the power supply 142 includes one or more batteries or battery packs, as illustrated in FIG. 8.

In some embodiments, the batteries are replaceable alkaline batteries (for example AA or AAA batteries) or are a type of rechargeable battery. Rechargeable batteries include, for example, lithium-ion, lead-acid, nickel cadmium, nickel metal hydride, etc. Lithium-ion batteries are generally smaller and lighter than conventional lead-acid batteries, which may enable the system 1 to be smaller and lighter. In other embodiments, the power supply 142 includes supply connections (not illustrated). The supply connections allow the rechargeable batteries to recharge when the base assembly 10 is connected to an external electrical supply. For example, the external electrical supply may be an outlet or charger, portable or otherwise. Alternatively, the system 1 may include QI standard coils to permit inductive recharging, such that no supply connections are required. If the system 1 were to include QI standard coils, the base assembly 10 may be placed on a base station for recharging the one or more batteries. As a result of using inductive recharging methods, the system may further inhibit cross-contamination. The QI standard coils may further be in communication with separate communication modules, which may be external to the system 1 and/or the base station, and the user interface. For example, the signals may include information, data, serial data, and/or data packets, among other things. The communication module can be coupled to one or more separate communication modules via wires, fiber, and/or wirelessly. Communication via wires and/or fiber can be any appropriate network topology known to those skilled in the art. For example, wired and/or fiber communication may take place over Ethernet. Wireless communication can be any appropriate wireless network topology known to those skilled in the art. For example wireless communication may take place over Wi-Fi, Bluetooth, Zig-Bee, Z-Wave, and/or ANT, among other things.

To preserve power, the system 1 may be configured to start a sleep timer after a predetermined time of inactivity (e.g., 20 minutes without user interaction with the device). If the sleep timer expires, the device can turn off to preserve power.

The electrical pulses used by the system 1 to effect transfection of the cells in the skin tissue (i.e., electroporation) are any known pulse patterns. In particular the pulse pattern can be a square wave pulse. In some embodiments, the electroporation pulse generator can deliver an electric pulse to the desired tissue at voltage levels of about 0.01 V to about 70) V, about 0.01 V to about 50 V, about 0.01V to about 40 V, about 0.01V to about 30) V, about 0.01V to about 20 V, about 0.01V to about 15 V, about 0.1 V to about 70 V, about 0). 1 V to about 50 V, about 0). 1 V to about 40) V, about 0.1 V to about 30 V, about 0.1V to about 25 V. and about 0.1V to about 15 V. In particular, the electrical pulse may be about 10 V to about 25 V. In some embodiments, the present disclosure delivers electrical energy that is characterized by an electrical pulse delivering current into the desired tissue at about 0.02 mA to about 100 mA, about 0.1 mA to about 100 mA, about 0.2 mA to about 100 mA, about 0.5 mA to about 100 mA, about 1 mA to about 100 mA, about 1 mA to about 80 mA, about 1 mA to about 60 mA, about 1 mA to about 50 mA, about 1 mA to about 40 mA, and about 1 mA to about 30 mA. In particular, the current delivered may be about 1 mA to about 100 mA, or about 1 mA to about 30 mA, or 10 mA.

The electrical pulses associated with the present disclosure will generally be characterized by the short duration of each pulse, including pulse lengths of about 5 msec to about 250 msec, about 10 msec to about 250 msec, about 20 msec to about 250 msec, about 40 msec to about 250 msec, about 60 msec to about 250 msec, about 80 msec to about 250 msec, about 100 msec to about 250 msec, about 20 msec to about 200 msec, about 40 msec to about 200 msec, about 60 msec to about 200 msec, about 80 msec to about 200 msec, about 100 msec to about 200 msec, about 20 msec to about 150 msec, about 40 msec to about 150 msec, about 60 msec to about 150 msec, about 80 msec to about 150 msec, about 100 msec to about 150 msec, about 100 msec to about 140 msec, about 100 msec to about 130 msec, about 100 msec to about 120 msec, and about 100 msec to about 110 msec. In particular, the electrical pulse length may be about 100 msec. The electrical pulses may be followed by a delay in advance of the next pulse. The delay may be about 5 msec to about 250 msec, about 10 msec to about 250 msec pulse, about 20 msec to about 250 msec, about 40 msec to about 250 msec, about 60 msec to about 250 msec, about 80 msec to about 250 msec, about 100 msec to about 250 msec, about 20 msec to about 200 msec, about 40 msec to about 200 msec, about 60 msec to about 200 msec, about 80 msec to about 200 msec, about 100 msec to about 200 msec, and about 150 msec to about 200 msec. In particular, the delay may be about 200 msec. The electric pulses delivered are repeated to deliver a number of pulses for each vaccination. For example, the number of electric pulses delivered may be 1, 2, 3, 4, 5, 6, 7, 8, 9, or 10. In particular, the number of electric pulses may be from 1-6 pulses, or 2 or 3 pulses.

The cartridge 120 may include an identification system to allow the device to verify the contents of the cartridge 120 before an injection can occur. Specifically, the cartridge 120 may include an embedded RFID tag or other label (not illustrated) readable by the controller when the cartridge 120 is installed in the array 82. In such instances, the controller would verify the proper cartridge 120 is in place before allowing the injection to take place. In some embodiments (e.g., a standalone EP system), the system 1 may function without a cartridge 120.

The present disclosure is configured to increase the immune response by at least about 5%, about 10%, about 20%, about 30%, about 40%, about 50%, about 60%, about 70%, about 80%, about 90%, about 100%, about 110%, about 120%, about 130%, about 140%, about 150%, about 160%, about 170%, about 180%, about 190%, about 200%, about 220%, about 230%, about 240%, about 250%, about 260%, about 270%, about 280%, about 290%, about 300%, about 310%, about 320%, about 330%, about 340%, about 350%, about 360%, about 370%, about 380%, about 390%, about 400%, about 410%, about 420%, about 430%, about 440%, about 450%, about 460%, about 470%, about 480%, about 490%, or about 500%, about 550%, about 600%, about 650%, about 700%, about 750%, about 800%, about 850%, about 900%, about 950%, about 1000%, about 1100%, about 1200%, about 1300%, about 1400%, about 1500%, about 1600%, about 1700%, about 1800%, about 1900%, about 2000%, about 2100%, about 2200%, about 2300%, about 2400%, about 2500%, about 2600%, about 2700%, about 2800%, about 2900%, or about 3000% over a naïve subject.

In another embodiment, the present disclosure may increase the immune response at least about 1.25-fold, at least about 1.5-fold, at least about 2-fold, at least about 3-fold, at least about 4-fold, at least about 5-fold, at least about 8-fold, and at least about 10-fold, at least about 12-fold, at least about 14-fold, at least about 16-fold, at least about 18-fold, at least about 20-fold, at least about 25-fold or at least about 30-fold over a naïve subject.

In operation, to treat a subject, the user must first obtain the needle-free injection system 1 and at least one of the pre-filled cartridges 120 containing the proper agent and dosage. As the system 1 powers up, the system 1 may perform a number of self-tests, including software tests (e.g., a switching matrix internal test load) to assure the system 1 is ready for treatment and verifying the proper cartridge 120 is in place before allowing the injection to take place. With the initial setup complete, the user may then insert the cartridge 120. To insert the cartridge 120, the user either obtains a new unused jet injection module 40 or can remove the jet injection module 40 from the base assembly 10 to provide access to the cavity 18 at the lower end 14 of the housing 16 and the opening 45 at the upper end 44 of the injection housing 42 of the injection module 40. The user orients the cartridge 120 so that it is coaxial with the injection module 40 with the second end 125 closest to the beveled proximal end 50 of the nozzle 48. The user then axially introduces the cartridge 120 into the jet injection module 40 until the septum 121 is contacted and ultimately pierced by the beveled proximal end 50 of the nozzle 48, so that the nozzle 48 is in fluid communication with the volume 126 of the cartridge 120. In advance of reattaching the injection module 40 to the housing 16 with the cartridge 120, so the plunger 122 is coaxially aligned with the propulsion rod 62, the propulsion rod 62 is to be locked in place as detailed below. The user may then begin the jet injection and electroporation procedure.

Prior to operably coupling the injection module 40 to housing 16, the user applies a rotational force to the rotational knob 30 thereby compressing the propulsion spring 66 until the large section 172 of the slot 78 is moved over the trigger pin 67. As explained above, the leaf spring 69 urges the second portion 156 of the trigger pin 67 into the large section 172 of the slot 78 to lock the propulsion rod 62 in place. The user can then operably couple the injection module 40 to the base assembly 10, locate the desired tissue on the subject to receive the jet injection and electroporation, and bring the edge 43 of the injection module 40 in contact with the skin 2 of the subject. Subsequently, the user engages the push button 26 which moves the trigger pin 67 so that the small section 154 is now positioned within the slot 78. No longer being restricted, the propulsion spring 66 decompresses so that the propulsion rod 62 engages the plunger 122, providing an injection force that is coaxial with the first axis A The plunger head 127 moves through the volume 126 of the cartridge 120, ultimately deploying the dosage through the nozzle 48, the first orifice 96, and the second orifice 86 to the subject's skin 2. Simultaneously, the protrusion 155 contacts the microswitch 128 that engages the PCB 136 to initiate a timing sequence, such that upon completion of the timing sequence (which allows the jet injection to be completed), the electroporation is initiated as prescribed for that particular treatment. As explained above, EP array assembly 80 is deployed by the propulsion rod 62. The release pins 91 contact the latch detents 93, allowing the EP array assembly 80 to deploy. The electrodes 110 penetrate the epidermal tissues of the subject's skin 2 at depths up to about to about 1.0 mm, as illustrated in FIG. 11. After the timer has ended, the controller emits a signal for the power supply 142 to send a current to the contacts 140. The current continues from the contacts 140 to the contacts 100 of the flex circuit 83 and finally to the electrodes 110 where electroporation of the subject's skin 2 commences according to the predetermined parameters (e.g., the amount of time and number of pulses). As described above, the controller may continue to emit signals to the power supply 142 to continue electroporating the subject's skin 2.

An annunciator and/or LED's (not illustrated) can indicate the completion of electroporation and the system 1 is removed from the subject's skin 2, where the user can remove and replace the jet injection module 40 with a new pre-locked module 40 or the user can manually rearm or re-cock the system 1 for use by pushing the EP array assembly 80 back into the retracted position so that the latches 90 couple to the latch detents 93.

One of ordinary skill in the art understands that numerous changes and modifications of the EP devices, as explained above, may be made without departing from the spirit and the scope of the present disclosure.

EXAMPLES

Example 1. This example compares rat b cell responses generated by the use of influenza pNP (pGX2013) and RSV-F (pGX2303) delivered to the skin by: (1) Mantoux injection in combination with skin electroporation (SEP); (2) jet injection in combination with SEP; and (3) no treatment.

Methods: For the study three groups of rats were immunized: two groups of 10 female Wistar rats (8 weeks old) were immunized with pGX2013 and pGX2303 at separate abdominal skin flanks, and a group of 2 naïve (no treatment) female Wistar rats (8 weeks old) group. Immunizations were performed on day 1 and day 15. The treatment was done by injection of 50 ug pGx2303/15 ug pGX2013 in 50 uL PBS ID (abdominal flank, separate locations for each plasmid (pGx2303 injected into left flank and pGX2013 injected into right flank)) administered either with the ID jet injection device (Biojector R. 2000, available from Bioject Medical Technologies, Inc, Tigard, OR) or Mantoux injection (using a 29 gauge Insulin syringe) and SEP was performed immediately after each injection. Skin electroporation performed using 25V, 100 msec per pulse with 200 msec delay between pulses (square pulse waveform) and current was capped at 0.5 A.

ELISA: Rats were bled by the jugular sampling technique on days 15 and 22. Ninety-six (96)-well flat-bottom plates (Costar 3590) were coated overnight at 4° C. with 300 ng I ml of Influenza NP (IMR-274, available from Novus Biologicals) or Hu RSV-F (11049-V08B, available from Sinobiologicals). Plates were washed ×4 using an automatic plate wash (wash solution PBS with 0.05% Tween-20), and blocked with 3% BSA PBS 0.05% Tween-20 buffer for two hours at 37° C. The plates were washed and 100 uL aliquots of sera starting at a 1:50 serial dilution in 1% BSA PBS 0.05% Tween-20 buffer were added in triplicate and incubated for 2 hours at 37° C. The plates were washed and 100 uL of goat anti-rat IgG-HRP (Sigma cat #A9037) at a 1:10,000 dilution was added for 1 hour at 37° C. The plates were washed and developed using a two component (50 ul of each/well) TMB microwell peroxidase system (Cat #50-76-00, available from Kirkegaard & Perry Laboratories) for 6 minutes at room temperature before stop solution (50 ul)

was added. OD450 measurements were acquired using Molecular Devices SpectraMax 384 and end point titer cutoffs were calculated based on an OD450 reading of twice the PBS background.

Results: As shown in FIGS. 21A-B and 22A-B, the combination of jet injection plus electroporation resulted in a more rapid immune response being elicited as shown by higher antibody responses at day 15 and/or day 22 (post-immunization) for both the influenza pNP (pGX2013) and RSV-F (pGX2303) delivered to the skin when compared to the Mantoux injection plus electroporation.

Example 2. A second experiment was performed using new Wistar rats grouped as identified above and according to the immunization, SEP and ELISA methods as set forth in Example 1.

Results: As shown in FIGS. 23A-B and FIGS. 24A-B, the combination of jet injection plus electroporation resulted in a more rapid immune response being elicited as shown by higher antibody responses at day 15 and/or day 22 (post-immunization) for both the influenza pNP (pGX2013) and RSV-F (pGX2303) delivered to the skin when compared to the Mantoux injection plus electroporation.

For reasons of completeness, various aspects of the invention are set out in the following numbered clauses:

Clause 1. An electroporation device for use with an agent cartridge defining a volume containing a pre-measured dose of agent therein, the electroporation device comprising:
- a housing having an axis extend therethrough;
- a nozzle at least partially positioned within the housing;
- a cavity sized to receive at least a portion of the agent cartridge therein, and wherein the nozzle is in fluid communication with the volume of the agent cartridge when the agent cartridge is positioned within the cavity;
- an array having a plurality of electrodes extending therefrom;
- a propulsion cartridge configured to operatively engage the agent cartridge when the agent cartridge is positioned within the cavity; and
- a power supply in electrical communication with the array.

Clause 2. The electroporation device of clause 1, wherein the propulsion cartridge is adjustable between an armed configuration and a deployed configuration, and wherein the propulsion cartridge is biased toward the deployed configuration.

Clause 3. The electroporation device of clause 2, wherein adjusting the propulsion cartridge from the armed configuration to the deployed configuration mechanically expels a portion of the pre-measured dose of agent through the nozzle.

Clause 4. The electroporation device of clause 2, further comprising a trigger, and wherein the trigger is adjustable between a first position, where the propulsion cartridge is fixed in the armed configuration, and a second position, where the propulsion cartridge is adjustable between the fixed and deployed configurations.

Clause 5. The electroporation device of clause 4, wherein the trigger is adjustable between the first position, where the array is in electrical communication with the power supply, and the second position, where the array is not in electrical communication with the power supply.

Clause 6. The electroporation device of clause 1, wherein the array is axially moveable with respect to the housing between a retracted position, where the electrodes are positioned inside the housing, and an extended position, where at least a portion of the electrodes are positioned outside the housing.

Clause 7. The electroporation device of clause 6, wherein the array is biased toward the extended position.

Clause 8. The electroporation device of clause 6, further comprising a trigger, and wherein the trigger is adjustable between a first position, where the array is fixed in the retracted position, and a second position, where the array is movable between the retracted and extended positions.

Clause 9. The electroporation device of clause 8, wherein the propulsion cartridge is adjustable between an armed configuration and a deployed configuration, and wherein the trigger is adjustable between the first position, where the propulsion cartridge is fixed in the armed configuration, and the second position, where the propulsion cartridge is adjustable between the armed and deployed configurations.

Clause 10. The electroporation device of clause 1, further comprising a signal generator in electrical communication with both the power supply and the array, wherein the signal generator is configured to receive electrical power from the power supply and output an electroporation signal to the array.

Clause 11. An electroporation device for use with an agent cartridge defining a volume containing a pre-measured dose of agent therein, the electroporation device comprising:
- a housing defining a cavity sized to receive at least a portion of the agent cartridge therein;
- a nozzle at least partially positioned within the housing and in fluid communication with the agent cartridge when the cartridge is positioned within the cavity;
- a propulsion rod positioned at least partially within the housing and movable with respect thereto between an armed position and a deployed position, and wherein movement of the propulsion rod from the armed position to the deployed position expels at least a portion of the pre-measured dose of agent through the nozzle;
- a propulsion spring extending between the propulsion rod and the housing, the propulsion spring configured to bias the propulsion rod toward the deployed position;
- an array having one or more electrodes extending therefrom; a power supply; and
- a trigger assembly adjustable between a first configuration, where the propulsion rod is fixed in the armed position and the power supply is not in electrical communication with the array, and a second position, where the propulsion rod is free to move between the armed and deployed positions and the power supply is in electrical communication with the array.

Clause 12. The electroporation device of clause 11, wherein the nozzle includes a first end positioned proximate a first end of the housing, and a second end in fluid communication with the volume of the agent cartridge.

Clause 13. The electroporation device of clause 11, further comprising a signal generator and a switch, wherein the signal generator is at least partially controlled by the switch, and wherein the signal generator is configured to receive electrical power from the power supply and output an electroporation signal to the array.

Clause 14. The electroporation device of clause 13, wherein the switch is at least partially controlled by the trigger assembly.

Clause 15. The electroporation device of clause 11, wherein the array is movable with respect to the housing moveable with respect to the housing between a retracted position, where the electrodes are positioned inside the housing, and an extended position, where at least a portion of the electrodes are positioned outside the housing.

Clause 16. The electroporation device of clause 15, wherein the array includes one or more latches to releasably engage the housing, and wherein the latches are configured to fix the array in the retracted position.

Clause 17. The electroporation device of clause 11, further comprising an arming cam configured to move the propulsion rod from the relaxed position to the armed position.

Clause 18. The electroporation device of clause 15, wherein the array includes one or more latches configured to releasably engage the housing, wherein the latches retain the array in the retracted position.

Clause 19. An electroporation device comprising:
a cartridge defining a volume having a pre-measured dose of agent therein, at least a portion of the volume being sealed off by a plunger;
a jet injection module including;
a first housing defining a cavity sized to receive at least a portion of the cartridge therein,
a nozzle at least partially positioned within the housing and in fluid communication with the cartridge when the cartridge is positioned within the cavity, and
an array having one or more electrodes extending therefrom, wherein the array is movable with respect to the first housing between a retracted position, where the electrodes are positioned within the housing, and an extended position, where at least a portion of the electrodes are positioned outside the housing; and
a base assembly being removably couplable to the jet injection module, the base assembly including;
a propulsion rod positioned at least partially within the housing and movable with respect a thereto between an armed position and a deployed position, and wherein the propulsion rod is configured to operatively engage the cartridge,
a propulsion spring extending between the propulsion rod and the housing, the propulsion spring configured to bias the propulsion rod toward the deployed position;
a power supply, and
a trigger assembly adjustable between a first configuration, where the propulsion rod is fixed in the armed position and the power supply is not in electrical communication with the array, and a second position, where the propulsion rod is free to move between the armed and deployed positions and the power supply is in electrical communication with the array.

Clause 20. The electroporation device of clause 19, wherein the trigger assembly is adjustable between the first configuration, where the array is fixed in the retracted position, and the second configuration, where the array is movable between the retracted and extended positions.

The invention claimed is:

1. A jet injection module for an electroporation device, the jet injection module comprising:
a housing defining a cavity, wherein the cavity is sized to receive at least a portion of an agent cartridge therein;
a mounting body coupled to the housing within the cavity; and
a nozzle removably coupled to the mounting body such that, when the nozzle is coupled to the mounting body and the mounting body is coupled to the housing, the nozzle is at least partially positioned within the housing, wherein a distal end of the nozzle includes a nozzle tip configured to deliver a jet injection of agent delivered from the agent cartridge.

2. The jet injection module of claim 1, wherein the cavity of the housing is configured to receive an agent cartridge containing a volume of the agent, and a proximal end of the nozzle is configured to penetrate a septum of the agent cartridge when the agent cartridge is inserted in the cavity.

3. The jet injection module of claim 2, wherein the proximal end of the nozzle is beveled.

4. The jet injection module of claim 1, wherein the mounting body is a spider clamp.

5. The jet injection module of claim 1, wherein the mounting body is releasably coupled to the housing by a fastener.

6. The jet injection module of claim 1, further comprising an array having a plurality of electrodes extending therefrom, wherein the array is mounted to a support slide that is axially moveable with respect to the housing and the nozzle between a retracted position, where the electrodes are positioned inside the housing, and an extended position, where at least a portion of the electrodes are positioned outside the housing.

7. The jet injection module of claim 6, further comprising an array spring that biases the support slide.

8. The jet injection module of claim 7, wherein the array spring biases the support slide toward the extended position.

9. The jet injection module of claim 8, wherein at least a portion of the array spring is positioned about mounting body, and the array spring is configured to abut a portion of the housing.

10. The jet injection module of claim 8, wherein the array includes one or more latches configured to releasably engage the housing, and wherein the one or more latches are configured to fix the array in the retracted position.

11. The jet injection module of claim 10, wherein the housing defines one or more interior recesses each having a latch detent, and the one or more latches are configured to engage the associated latch detent when fixed in the retracted position.

12. A jet injection module for an electroporation device, the jet injection module comprising:
a housing defining a cavity, wherein the cavity is sized to receive at least a portion of an agent cartridge therein;
a mounting body coupled to the housing within the cavity; and
a nozzle removably coupled to the mounting body such that, when the nozzle is coupled to the mounting body and the mounting body is coupled to the housing, the nozzle is at least partially positioned within the housing, wherein a distal end of the nozzle includes a nozzle tip configured to deliver a jet injection of agent delivered from the agent cartridge,
wherein the mounting body is releasably coupled to the housing within the cavity, so that the mounting body can be removed from the housing and the nozzle can be interchanged with a replacement nozzle in the mounting body, and the mounting body can be recoupled to the housing.

13. The jet injection module of claim 12, wherein the mounting configuration is configured such that the nozzle is interchangeable in the mounting body with a variety of nozzles having different configurations.

14. The jet injection module of claim 13, further comprising the variety of nozzles, wherein the variety of nozzles have different tip configurations for allowing a jet stream to be applied to a tissue surface in differing patterns.

15. The jet injection module of claim 13, wherein the variety of nozzles provide different distances between the nozzle tip and the tissue surface of a patient.

16. The jet injection module of claim 15, wherein the distances vary from about 0.5 cm to about 2.0 cm.

17. The jet injection module of claim 13, wherein the variety of nozzles have different diameters of the nozzle tip.

18. The jet injection module of claim 13, wherein the variety of nozzles have different internal funneling configurations.

19. The jet injection module of claim 18, wherein at least one of the internal funneling configurations causes the jet stream to have a laminar flow.

20. The jet injection module of claim 18, wherein at least one of the internal funneling configurations causes the jet stream to have a turbulent flow.

21. The jet injection module of claim 13, wherein at least one of the variety of nozzles has multiple orifice outlets configured to increase distribution of the agent in tissue.

22. A jet injection module for an electroporation device, the jet injection module comprising:

a housing defining a cavity, wherein the cavity is sized to receive at least a portion of an agent cartridge therein;
   a mounting body coupled to the housing within the cavity, wherein the mounting body is frictionally coupled to the housing within the cavity; and
   a nozzle removably coupled to the mounting body such that, when the nozzle is coupled to the mounting body and the mounting body is coupled to the housing, the nozzle is at least partially positioned within the housing, wherein a distal end of the nozzle includes a nozzle tip configured to deliver a jet injection of agent delivered from the agent cartridge.

23. The jet injection module of claim 22, wherein the mounting body is frictionally coupled by compression fitting to the housing.

24. The jet injection module of claim 23, wherein the compression fitting substantially holds the mounting body in place relative to the housing during the jet injection.

\* \* \* \* \*